US007884099B2

(12) United States Patent  
Ding et al.

(10) Patent No.: US 7,884,099 B2  
(45) Date of Patent: Feb. 8, 2011

(54) QUINOLONE CARBOXYLIC ACID-SUBSTITUTED RIFAMYCIN DERIVATIVES

(75) Inventors: Charles Z. Ding, Foster City, CA (US); Yafei Jin, Ann Arbor, MI (US); Keith Combrink, Arlington, TX (US); In Ho Kim, Dublin, OH (US)

(73) Assignee: Cumbre IP Ventures, L.P., Dallas, TX (US)

( * ) Notice: Subject to any disclaimer, the term of this patent is extended or adjusted under 35 U.S.C. 154(b) by 218 days.

(21) Appl. No.: 12/269,652

(22) Filed: Nov. 12, 2008

(65) Prior Publication Data  
US 2009/0143373 A1 Jun. 4, 2009

Related U.S. Application Data

(60) Provisional application No. 61/003,549, filed on Nov. 16, 2007.

(51) Int. Cl.  
*C07D 491/20* (2006.01)  
*C07D 498/16* (2006.01)  
*A61K 31/498* (2006.01)  
*A61K 31/5383* (2006.01)

(52) U.S. Cl. ................ 514/229.5; 514/278; 544/99; 546/17

(58) Field of Classification Search .......... 544/99; 546/17; 514/229.5, 278  
See application file for complete search history.

(56) References Cited

U.S. PATENT DOCUMENTS

| 4,165,317 | A | 8/1979 | Rossetti et al. |
| 4,219,478 | A | 8/1980 | Marsili et al. |
| 4,563,459 | A | 1/1986 | Grohe et al. |
| 4,620,007 | A | 10/1986 | Grohe et al. |
| 4,983,602 | A | 1/1991 | Yamane et al. |
| 5,880,283 | A | 3/1999 | Matsumoto et al. |
| 2005/0137189 | A1 | 6/2005 | van Duzer et al. |
| 2005/0209210 | A1 | 9/2005 | Ding et al. |
| 2005/0256096 | A1 | 11/2005 | Combrink et al. |
| 2005/0261262 | A1 | 11/2005 | Ma et al. |
| 2006/0019985 | A1 | 1/2006 | Ma et al. |
| 2006/0019986 | A1 | 1/2006 | Ding et al. |

FOREIGN PATENT DOCUMENTS

| EP | 0 333 176 A2 | 9/1989 |
| GB | 1 603 127 A | 11/1981 |
| WO | WO 02/102792 A1 | 12/2002 |
| WO | WO 03/045319 A2 | 6/2003 |
| WO | WO 2006/012443 A1 | 2/2006 |
| WO | WO 2007/056086 A2 | 5/2007 |
| WO | WO 2007/070613 A2 | 6/2007 |

OTHER PUBLICATIONS

Hamilton-Miller, JMT, "Dual-action antibiotic hybrids" Journal of Antimicrobiol Chemotherapy, 1994, vol. 33, No. 2, pp. 197-200, US.

International Search Report, European Patent Office, Mar. 4, 2009.

Farr, B. M., Rifamycins, in Principles and Practice of Infectious Diseases, Mandell, G. L., Bennett, J. E., Dolin, R., Eds.; Churchhill Livingstone: Philadelphia; p. 348-361, 2000.

Helv. Chim. Acta., 1973, 56, p. 2369.

European Patent Office, International Preliminary Report on Patentability, Serial No. PCT/US2008/083246, Feb. 15, 2010.

Karchmer, A. W. et al: "Rifampin treatment of Prosthetic Valve Endocarditis Due to Staphylococcus epidermidis" Rev. Infect. Dis. 5 (S3): p. S543-548 (1983).

Kaufman C. A. et al: "Increasing resistance of *Staphylococcus aureus* to ciprofloxacin" Antimicrob Agents Chemother. Sep. 1990 34(9):1862-3.

National Committee for Clinical Laboratory Standards, Methods for dilution antimicrobial susceptibility tests for bacteria that grow aerobically, 5th ed. M7-A5. National Committee for Clinical Laboratory Standards, Wayne, PA 2000.

Watanakunakorn, C, "Interaction of Vancomycin and Rifampin Against *Staphyloccocus aureus*," Antimicrob. Agents & Chemother. 19(6): p. 1089-1091 (1981).

Yajko, D. M. et al: "In Vitro Susceptibility of *Mycobacterium* avium Complex to the New Fluoroquinolone Sparfloxacin and Comparison with Ciprofloxacin" Antimicrob. Agents & Chemother. 34(12): p. 2442-2444 (1990).

*Primary Examiner*—Bruck Kifle  
(74) *Attorney, Agent, or Firm*—Jackson Walker L.L.P.

(57) ABSTRACT

The compounds include substituted rifamycin derivatives in which a quinolone carboxylic acid pharmacophore is covalently bonded to a benzoxazinorifamycin or a spiropiperidinorifamycin. The rifamycin derivatives are useful as antimicrobial agents and are effective against a number of human and veterinary Gram positive and Gram negative pathogens. The advantage of the inventive compounds is that both the rifamycin and quinolone antibacterial pharmacophores are co-delivered with matched pharmacokinetics to the targeted pathogens of interests. Delivery of multiple antibacterial pharmacophores simultaneously to the targeted pathogens has the maximum chance of achieving synergy and minimizing the development of resistance to the antibiotics given.

6 Claims, 2 Drawing Sheets

QUINOLONE CARBOXYLIC ACID-SUBSTITUTED RIFAMYCIN DERIVATIVES

This application claims priority to U.S. Provisional Patent Application Ser. No. 61/003,549, entitled "QUINOLONE CARBOXYLIC ACID-SUBSTITUTED RIFAMYCIN DERIVATIVES" filed on Nov. 16, 2007, the entire content of which is hereby incorporated by reference.

BACKGROUND

The present invention relates to quinolone carboxylic acid-substituted rifamycin derivatives wherein a quinolone carboxylic acid antibiotic pharmacophore is covalently and chemically combined with a 3,4-fused rifamycin: a 3,4-fused benzoxazinorifamycin or a 3,4-fused spiropiperidineimidazolorifamycin, resulting in a multifunctional antibiotic possessing multiple antibacterial pharmacophores.

The increasing spread in bacterial resistance to existing antibacterial agents is a major clinical problem. Accordingly, there is a need in the art for compounds, compositions, and methods of treating warm-blooded animals that suffer from bacterial infections and are resistant to conventional antibacterial treatments. Rifamycin class of natural product derived antibiotics, like rifampin, rifabutin and rifapetine are currently used for the treatment of tuberculosis and other microbial infections (Farr, B. M., Rifamycins). At present, one of the major problems associated with the rifamycin class of antimicrobial agents is the rapid development of bacterial resistance. Mutations in rifamycin's target RNA polymerase are mainly responsible for the high frequency of development of resistance. Consequently, rifamycins are currently used only in combination therapies to minimize the development of resistance to this class of drug. Unfortunately, some antibiotic combinations are antagonistic, such as the rifampin and vancomycin combination (Watanakunakorn, 1981), and the rifampin and sparfloxacin combination (Yajko, D. M. 1990). Furthermore, even with co-administration of other antibiotics, resistance development to rifamycin component is frequent (Karchmer, A. W. 1983).

The 7-substituted quinolone carboxylic acids are well known as quinolone class of anti-bacterial agents and as synthetic intermediates to related compounds. The quinolone antibacterials including ciprofloxacin (U.S. Pat. Nos. 4,563,459 and 4,620,007); gatifloxacin and moxifloxacin (U.S. Pat. No. 5,880,283) are widely prescribed in clinic. The widespread use of these agents has resulted in high rate of resistance to this class of agents (Kaufman C. A. 1990), so that the compounds which are effective against quinolone resistant bacteria are highly desired.

U.S. Pat. No. 4,983,602 discloses a series of 3,4-benzoxazinorifamycins with various substituted piperazine groups. U.S. Pat. No. 4,219,478 discloses a series of 3,4-spiropiperidino-rifamycins with various alkyl groups. Neither patents disclose quinolone carboxylic acid substituted-rifamycin derivatives, their antibacterial activities and use of them for the treatment of infections. Published United States Patent Application Nos. US2005/0209210, US2005/0261262, US 2006/0019985 and US 2006/0019986 describe quinolone carboxylic acid substituted-rifamycin derivatives, wherein a quinolone carboxylic acid is linked to a rifamycin at C-3 position of rifamycin core-structure through variety of linkers, but not to a 3,4-fused benzoxazinorifamycin or a spiropiperidinorifamycin. Therefore, none of the patents or patent applications mention the linking quinolone-3-carboxylic acids to a 3,4-fused benzoxazinorifamycins or a 3,4-fused spiropiperidinorifamycins and their antibacterial activity and use of them as antibacterial agents for the treatment of infections.

SUMMARY

The current invention describes compounds that link a quinolone carboxylic acid pharmacophore to a 3,4-fused benzoxazinorifamycin or a spiropiperidinorifamycin as shown in general formula (I). The present invention is directed to structurally novel compounds produced by covalently bonding an antibacterial pharmacophore from quinolone class of compounds to a rifamycin compound. The advantage of the inventive compounds is that the both rifamycin and quinolone antibacterial pharmacophores are co-delivered with matched pharmacokinetics to the targeted pathogens of interests. Delivery of multiple antibacterial pharmacophores simultaneously to the targeted pathogens has the maximum chance of achieving synergy and minimizing the development of resistance to the antibiotics given. The inventive rifamycin derivatives are useful as antimicrobial agents effective against a number of human and veterinary Gram positive, Gram negative pathogens, including the Staphylococci, for example *S. aureus*; Enterococci, for example *E. faecalis*; Streptococci, for example *S. pneumoniae*; Haemophilus, for example *H. influenza*; Moraxella, for example *M. catarrhalis*; and Escherichia for example *E. coli*; Mycobacteria, for example *M. tuberculosis*; Helicobacter, for example *H. pylori*; Clostridium, for example *C. difficile*; Bacteroides for example, *B. fragilis, B. vulgates*; intercellular microbes, for example *Chlamydia* and *Rickettsiae*; and *Mycoplasma*, for example *M. pneumoniae*, amongst others. The present invention also relates to pharmaceutical compositions containing the quinolone carboxylic acid-substituted rifamycin derivatives, and to methods of treating a bacterial infection using the pharmaceutical compositions containing inventive rifamycin derivatives.

The current inventive compounds are multifunctional antibiotics, which are inhibitors of three bacterial enzymes, RNA polymerase, DNA gyrase and topoisomerase, as shown by genetically-defined bacterial strains. Therefore the inventive compounds are distinctly different from the known rifamycin or the quinolone antibiotics prescribed in the clinic today in their mode of action. Additionally, the inventive compounds are surprisingly effective antibacterials against both rifamycin-resistant and quinolone-resistant strains of bacteria.

In its principle embodiment, the current invention provides a series of quinolone carboxylic acid-substituted rifamycin derivatives that are anti-infectives having antimicrobial activity represented by general formula I:

I

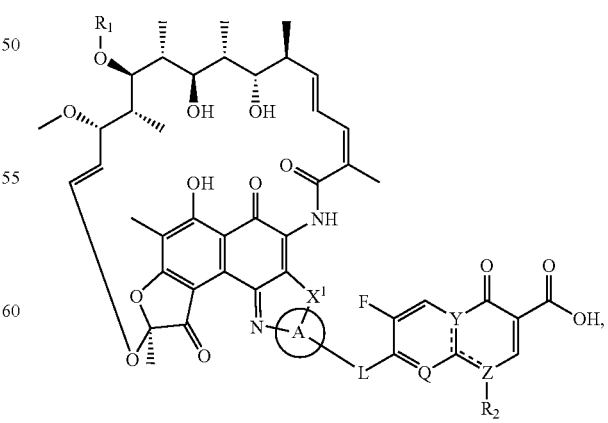

or a pharmaceutically acceptable salt thereof, wherein

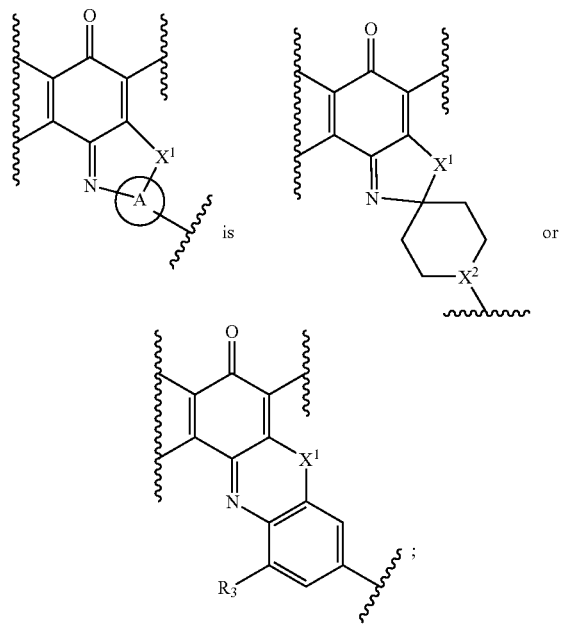

X¹ is NH, NR₄, O or S;

X² is N or CR₅;

L is a bond, or a linker group selected from one or a combination of two to three of the following groups:
1) (C₁-C₆)alkylene,
2) (C₃-C₈)cycloalkylene,
3) arylene,
4) heteroarylene,
5) heterocycloalkylene containing 1 to 3 heteroatoms,
6) —C(=O)—,
7) —C(=N—O—R₆)—,
8) —C=N—,
9) —O—
10) —S(O)$_n$—, wherein n is number between 0 and 2,
11) —N(R₇)—,
   wherein the carbon or nitrogen atoms of the linker "L" group are optionally substituted by 1 to 3 substituents selected from (C₁-C₆)alkyl, substituted (C₁-C₆)alkyl, amino, (C₁-C₆)alkylamino, di(C₁-C₆)alkylamino, hydroxyl, (C₁-C₆)alkoxy, and heterocycloalkyl group;

Q is N or CR₈;

Y and Z are independently selected from C or N;

R₁ is H or acetyl group;

R₂, R₄, R₅, R₆, R₇ are independently selected from hydrogen, (C₁-C₆)alkyl, (C₃-C₇)cycloalkyl, aryl, heteroaryl, and heterocycloalkyl groups that are all optionally substituted;

R₃ is 11, —OH or —SH; and

R₈ is H, F, Cl, CN, CH₃, OCH₃, OCHF₂ or CF₃.

Another aspect of the present invention is to provide a pharmaceutical composition containing a compound of formula (I) and a pharmaceutical acceptable carrier, diluent, or excipient useful as medicaments for the treatment and prevention of infections.

One other aspect of the present invention is to provide a method of treating bacterial infections in a mammal comprising administering to the mammal a pharmaceutically effective amount of a compound of formula (I) in a pharmaceutical composition as defined above.

DETAILED DESCRIPTION OF THE PREFERRED EMBODIMENTS

Figure 1:
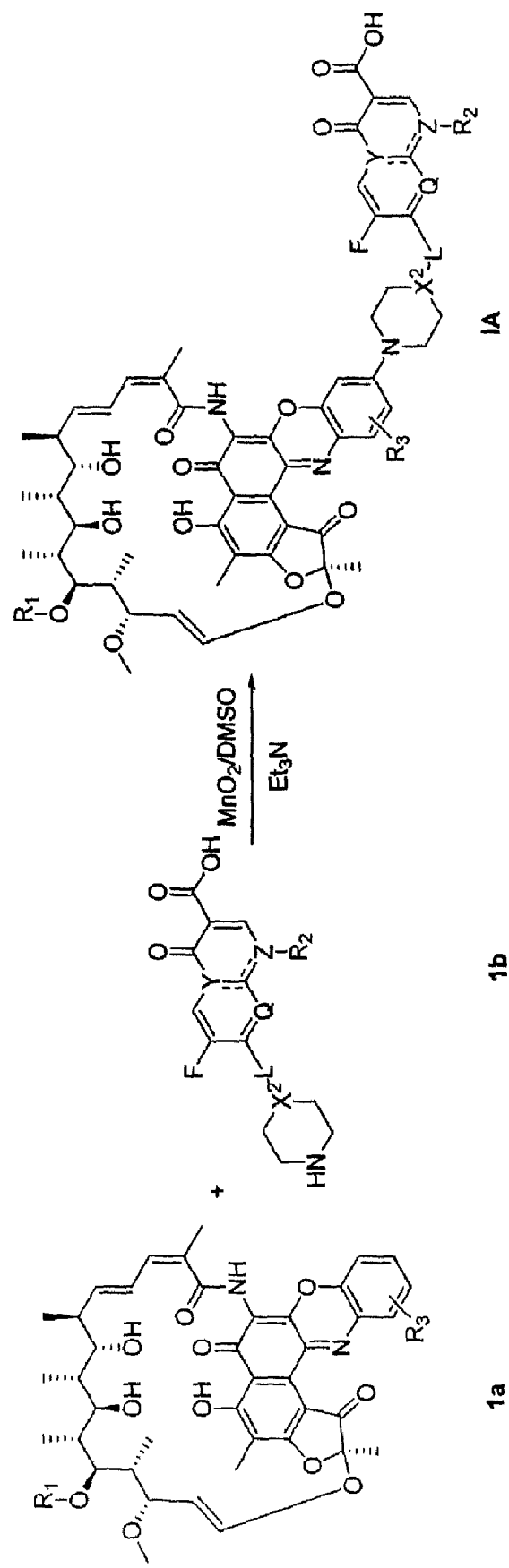
FIG. 1 shows a scheme for the general preparation of quinolone-substituted 3,4-fused benzoxazinorifamycins (IA).

As used herein, the terms and phrases have the meanings and definitions known in the art. Some of the more commonly used phrases are described in more detail below.

The term "alkyl," as used herein, refers to a monovalent, saturated, straight or branched chain hydrocarbon group. Examples of alkyl group include methyl, ethyl, propyl, iso-propyl, n-butyl, iso-butyl, tert-butyl, neo-pentyl, and n-hexyl. The alkyl groups of this invention can be optionally substituted.

The term "alkylene," as used herein, refers to bivalent saturated, straight or branched chain hydrocarbon structures. Examples of alkylene groups include methylene, ethylene, propylene, iso-propylene, n-butylene, isobutylene, and n-hexylene. The alkylene groups of this invention can be optionally substituted.

The term "alkylamino," as used herein, refers to an amino group (—NH₂), wherein one hydrogen atom is replaced by an alkyl group. Examples of alkylamino include methylamino, ethyl amino, propylamino, and isopropyl amino.

The term "alkylthio," as used herein, refers to an alkyl group, as defined herein, attached to the parent molecular group through a sulfur atom. Examples of alkylthio include methylthio, ethylthio, propylthio, and isopropylthio.

The term "alkoxy," as used herein, refers to an alkyl group, as previously defined, attached to the parent molecular group through an oxygen atom. Examples of alkoxy include methoxy, ethoxy, propoxy, iso-propoxy, n-butoxy, tert-butoxy, neo-pentoxy and n-hexoxy. The alkoxy groups of this invention can be optionally substituted.

The term "aryl" as used herein refers to a monovalent carbocyclic aromatic group including phenyl, naphthyl, and anthracenyl.

The term "arylene" as used herein refers to bivalent carbocyclic aromatic groups which can be optionally substituted.

The term "cycloalkyl," as used herein, refers to a monovalent saturated carbocyclic group having three to eight carbons such as cyclopropyl, cyclobutyl, cyclopentyl, cyclohexyl, cycloheptyl and cyclooctyl.

The term "cycloalkylene," as used herein, refers to bivalent saturated carbocyclic groups having three to eight carbons. The cycloalkylene groups can be optionally substituted.

The term "halogen," as used herein, refers to fluorine, chlorine, bromine and iodine atoms and the term "halo" refers to —F, —Cl, —Br, and —I as substituents.

The term "heteroaryl," as used herein, refers to a cyclic aromatic group having five or six ring atoms wherein at least one ring atom is selected from the group consisting of oxygen, sulfur, and nitrogen, and the remaining ring atoms are carbon. Heteroaryl groups of this invention include those derived from furan, imidazole, isothiazole, isoxazole, oxazole, pyrazine, pyrazole, pyridazine, pyridine, pyrimidine, pyrrole, quinoline, thiazole, 1,3,4-thiadiazole, triazole, and tetrazole.

The term "heteroarylene," as used herein, refers to a bivalent cyclic aromatic group having five or six ring atoms wherein at least one ring atom is selected from the group consisting of oxygen, sulfur, and nitrogen, and the remaining ring atoms are carbon. The heteroarylene group can be optionally substituted.

The term "heteroatom," as used herein, refers to oxygen, nitrogen or sulfur atom.

The term "heterocycloalkyl" as used herein, refers to a non-aromatic five-, six- or seven-membered ring or a bi- or tri-cyclic group having one or more heteroatoms independently selected from oxygen, sulfur and nitrogen wherein each 5-membered ring has zero to one double bonds and each six-membered ring has zero to 2 double bonds. The nitrogen and sulfur heteroatoms can optionally be oxidized, the nitrogen heteroatom can optionally be quaternized, and any of the above heterocyclic rings can be fused to an aryl or heteroaryl ring. Representative heterocycles include, but are not limited to: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, morpholinyl, isothiazolidinyl, and tetrahydrofurranyl. The heterocycloalkyl groups of this invention can be optionally substituted with one, two, or three substituents independently selected from —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -cycloheteroalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "heterocycloalkylene" as used herein, refers to a bivalent non-aromatic five-, six- or seven-membered ring having one or more heteroatoms independently selected from oxygen, sulfur and nitrogen wherein each 5-membered ring has zero to one double bonds and each six-membered ring has zero to 2 double bonds. The heterocycloalkylene groups of this invention can be optionally substituted.

The term "hydroxyl," as used herein, refers to —OH.

The term "protecting group", as used herein, refers to an easily removable group to which are known in the art to protect a functional group, such as hydroxyl and amino, against undesirable reaction during synthetic procedures and to be selectively removable. The use of protecting groups is well-known in the art for protecting groups against undesirable reactions during a synthetic procedure and many such protecting groups are known (Greene, 1991).

The term "substituted aryl," as used herein refers to an aryl group, as defined herein, substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, cycloalkyl, -heterocycloalkyl, —CF$_3$, —CH$_2$OH, —CH$_2$NH$_2$, -aryl, -heteroaryl, -benzyl, benzyloxy, -aryloxy, -heteroaryloxy, -alkoxy, -methoxymethoxy, -methoxyethoxy, amino, -benzylamino, -arylamino, -heteroarylamino, -alkylamino, -thio, -arylthio, heteroarylthio, -benzylthio, -alkylthio, or -methylthiomethyl.

The term "substituted heteroaryl" as used herein refers to a heteroaryl group as defined herein substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkyl thio, or -methylthiomethyl.

The term "substituted heterocycloalkyl," as used herein, refers to a heterocycloalkyl group, as defined above, substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl,-cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituent," as used herein, refers to —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO₂NH-alkyl, —SO₂NH-aryl, —SO₂NH-heteroaryl, -alkyl,-cycloalkyl, -heterocycloalkyl, —CF₃, —CH₂OH, —CH₂NH₂, -aryl, -heteroaryl, -benzyl, -benzyloxy, -aryloxy, -heteroaryloxy, -alkoxy, -methoxymethoxy, -methoxyethoxy, -amino, -benzylamino, -arylamino, heteroarylamino, -alkylamino, -thio, -arylthio, -heteroarylthio, -benzylthio, -alkylthio, or -methylthiomethyl.

The term "substituted," as used herein, refers to having substituent(s), as defined above, covalently attached.

The present invention is directed to quinolone carboxylic acid-substituted rifamycin hybrids of structural formula (I) as defined below:

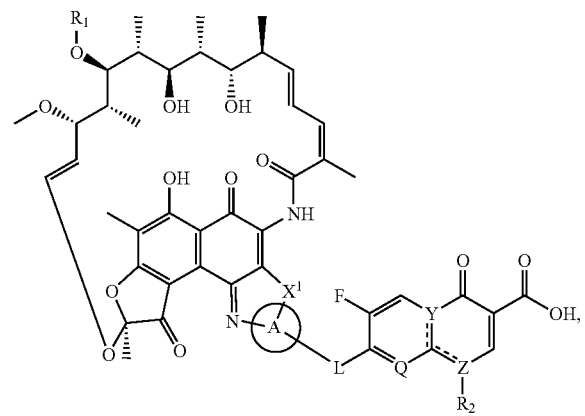

I or a pharmaceutically acceptable salt thereof,
wherein

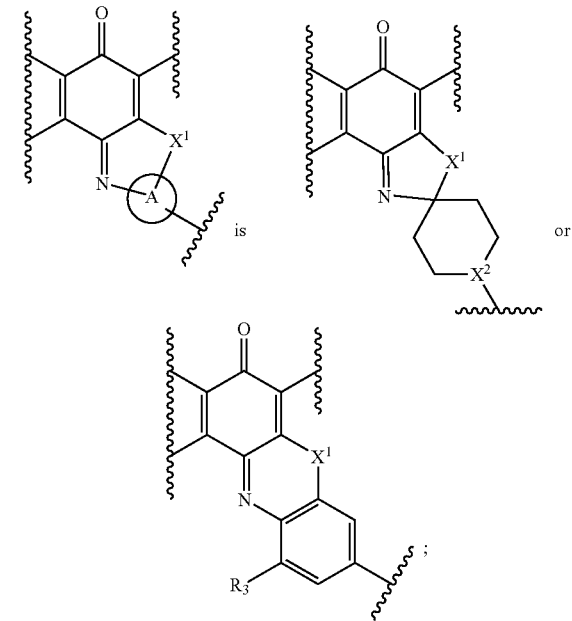

$X^1$ is NH, NR₄, O or S;

$X^2$ is N or CR₅;

L is a bond, or a linker group selected from one or a combination of two to five of the following groups:
1) (C₁-C₆)alkylene,
2) (C₃-C₈)cycloalkylene,
3) arylene,
4) heteroarylene,
5) heterocycloalkylene containing 1 to 3 heteroatoms,
6) —C(=O)—,
7) —C(=N—O—R₆)—,
8) —C=N—,
9) —O—,
10) —S(O)ₙ, wherein n is number between 0 and 2,
11) —N(R₇)—, wherein the carbon or nitrogen atoms of the linker "L" group are optionally substituted by 1 to 3 substituents selected from (C₁-C₆)alkyl, substituted (C₁-C₆)alkyl, amino, (C₁-C₆)alkylamino, di(C₁-C₆)alkylamino, hydroxyl, (C₁-C₆)alkoxy, and heterocycloalkyl group;

Q is N or CR₈;

Y and Z are independently selected from C or N;

R₁ is H or acetyl group;

R₂, R₄, R₅, R₆, R₇ are independently a group selected from hydrogen, (C₁-C₆)alkyl, (C₃-C₇)cycloalkyl, aryl, heteroaryl, and heterocycloalkyl groups that are all optionally substituted;

R₃ is H, —OH or —SH;

R₈ is H, F, Cl, CN, CH₃, OCH₃, OCHF₂ or CF₃.

Preferred compounds of the invention of formula (I) are those wherein:

L is a bond or a group selected from one or a combination of two to five groups

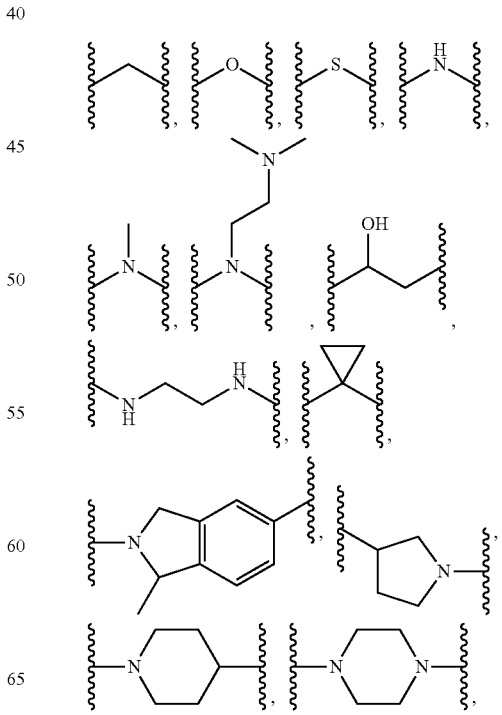

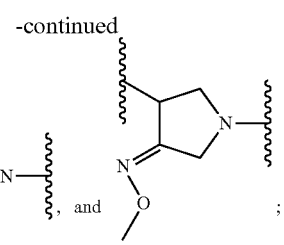

provided that the combination does not contain consecutive heteroatoms.

Yet, more preferred compounds of the present invention include the following named compounds:

a. (R)-5'-[3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-yl]-3'-hydroxy-benzoxazinorifamycin, b. (R)-5'-[4-[1-[1-(3-Carboxy-1-cyclopropyl-6-fluoro-8-methoxy-4-oxo-1,4-dihydro-quinoline-7-yl)-pyrrolidin-3-yl-cyclopropyl-methyl]-amino]-piperidin-1-yl]-3'-hydroxy-benzoxazinorifamycin, c. 5'-[4-(3-Carboxy-1-cyclopropyl-6-fluoro-8-methoxy-4-oxo-1,4-dihydroquinolin-7-yl)-piperazin-1-yl]-3'-hydroxy-benzoxazinorifamycin, d. 5'-[4-[1-(3-Carboxy-1-cyclopropyl-6-fluoro-8-methoxy-4-oxo-1,4-dihydro-quinoline-7-yl)-piperidin-4-yl-amino]-piperidin-1-yl]-3'-hydroxy-benzoxazinorifamycin, e. (R/S)-5'-[4-[[1-(1-Cyclopropyl-6-fluoro-8-methoxy-4-oxo-1,4-dihydro-quinolin-7-yl)-pyrrolidin-3-ylmethyl]-(2-dimethylamino-ethyl)-amino]-piperidin-1-yl]-3'-hydroxy-benzoxazinorifamycin, f. 4-Deoxy-3,4-[2-spiro-[1-(3-carboxy-1-cyclopropyl-6-fluoro-4-oxo-1,4-dihydroquinolin-7-yl)-piperidin-4-yl]]-(1H)-imidazo-(2,5-dihydro)rifamycin S, g. 4-Deoxy-3,4-[2-spiro-[1-(3-carboxy-1-cyclopropyl-6-fluoro-8-methoxy-4-oxo-1,4-dihydroquinolin-7-yl)-piperidin-4-yl]]-(1H)-imidazo-(2,5-dihydro)rifamycin S, and h. (R/S)-4-Deoxy-3,4-[2-spiro-[1-[1-(3-carboxy-1-cyclopropyl-6-fluoro-8-methoxy-4-oxo-1,4-dihydroquinolin-7-yl)-pyrrolidin-3-methyl]-piperidin-4-yl]]-(1H)-imidazo-(2,5-dihydro)rifamycin S.

Figure 2:
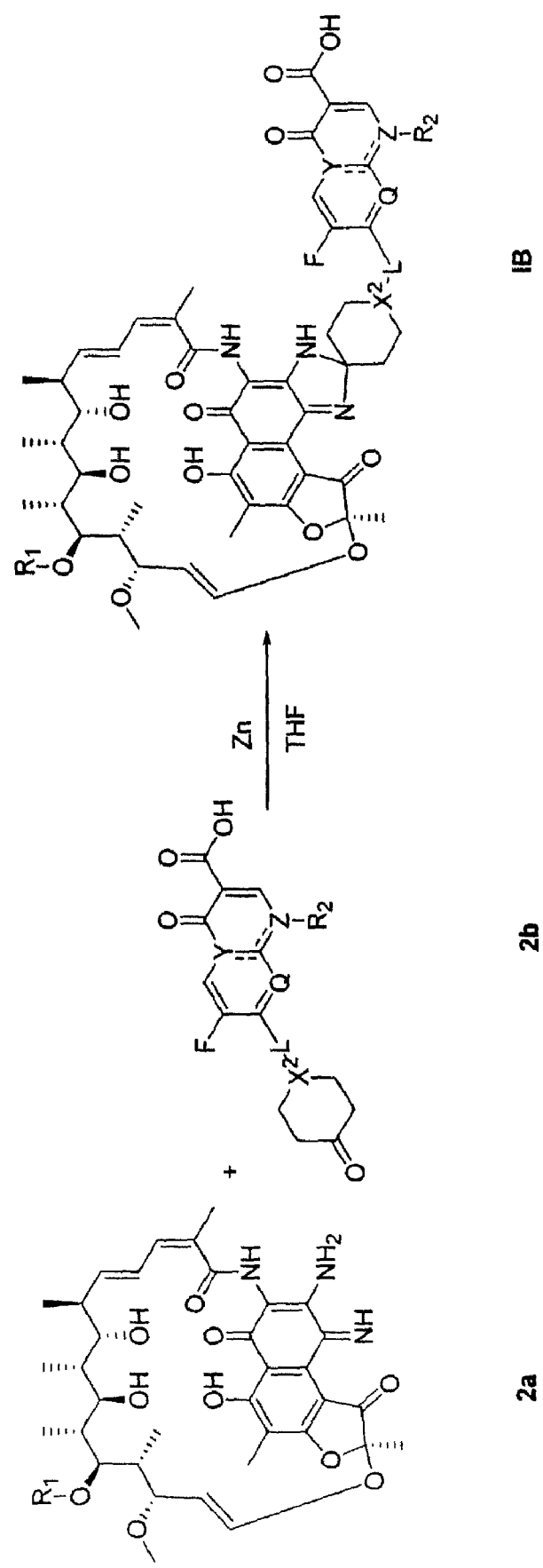
FIG. 2 shows a scheme for the general preparation of quinolone carboxylic acid-substituted spiropiperidinorifamycins (IB).

The inventive quinolone carboxylic acid-substituted rifamycin derivatives may be prepared as shown in the schemes illustrated in FIGS. 1-2. Scheme 1, shown in FIG. 1, shows general preparation of quinolone-substituted 3,4-fused benzoxazinorifamycins (IA). 3'-Hydroxy-benzoxazino-rifamycin (1a) prepared according to the procedure described in Helv. Chim. Acta. is reacted at a temperature ranging from 10° C. to 40° C. with a quinolone carboxylic acid possessing a nucleophilic amine (1b) in a solvent, such as DMSO, in the presence of a base, such as triethylamine or potassium carbonate, and an oxidant, such as $MnO_2$ to give quinolone carboxylic acid-substituted 3,4-fused benzoxazino-rifamycins (IA). The syntheses of quinolone carboxylic acids (1b) are known and described in the literature (e.g., published United States Application Publication Nos. US2005/0209210, US2005/0261262, US 2006/0019985 and US 2006/0019986).

Scheme 2, shown in FIG. 2, illustrates the general preparation of quinolone carboxylic acid-substituted spiropiperidinorifamycins (IB). 3-Amino-4-deoxy-4-imino-rifamycin S (2a) prepared by following a literature report (U.S. Pat. No. 4,017,481), is coupled to a quinolone carboxylic acid (2b) possessing a ketone functionality (eg: piperidone or hexanone-type) at a temperature ranging from 10° C. to 40° C. in organic solvent, such as THF or ethanol, in the presence or absence of a catalyst, such as Zinc. The syntheses of quinolone carboxylic acids (2b) are known and described in the literatures (e.g., published United States Application Publication Nos. US2005/0209210, US2005/0261262, US 2006/0019985 and US 2006/0019986).

The above syntheses schemes are preferred schemes for the synthesis of quinolone carboxylic acid-substituted rifamycin derivatives of formula (I). It is apparent to one skilled in art that other sequence of the reactions, and alternative reagents can be used for the synthesis of the inventive rifamycin derivatives. These alternatives for the synthesis of the inventive rifamycin derivatives are within the scope of this invention.

The quinolone carboxylic acid-substituted rifamycin derivatives of formula (I) of the present invention may contain chiral centers. The rifamycin portion of the inventive compounds are derived from natural product rifamycin and inherit chirality. The linkage group "L" and quinolone carboxylic acid pharmacophore may contain one or more chiral centers. It is apparent to one skilled in the art that when one chiral center is present in either "L" or the quinolone carboxylic acid pharmacophore, the chiral center can exist as one of two possible optical configurations ((R) and (S)). The resulting rifamycin derivative of the formula (I) can exist as one of the two possible diastereomers resulting from the two possible optical configurations, or a diastereomeric mixture of both. Both individual diastereomers and as well as mixtures thereof, are within the scope of the quinolone carboxylic acid-substituted rifamycin derivatives of formula (I) of the invention. The preferred compounds of the present invention are optically pure diastereomers having the (S) or (R)-configuration in either the "L" or quinolone carboxylic acid pharmacophore. It is known in the art that one diastereomer is superior to the other in activity. However, the racemic mixture also is useful, though a greater amount of the racemic material may be required to produce the same effect as the pure diastereomer.

If desired, the mixture of pure diastereomers is resolved by means known to those skilled in the art. Single pure material can be obtained by resolution of the diastereomeric mixture by crystallization, HPLC, or other methods. Alternatively, resolution of the racemic mixture can be accomplished by selective crystallization of a salt form using methods known to those skilled in the art.

A compound of formula (I), or a prodrug or a physiologically acceptable salt or solvate thereof, can be administered as the neat compound or as a pharmaceutical composition containing other inert entity.

The pharmaceutical compositions of the present invention can be prepared by admixing a compound of formula (I) with a solid or liquid pharmaceutically acceptable carrier, and, optionally, with pharmaceutically acceptable adjuvants and excipients employing standard and conventional techniques. Solid form compositions include powders, tablets, dispersible granules, capsules, cachets and suppositories. A solid carrier can be at least one substance, which also can function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, a low melting wax, cocoa butter, and the like. Liquid form compositions include solutions, suspensions, and emulsions. For example, compounds of the present invention can be dissolved in water, water-propylene glycol, or water-polyethylene glycol, optionally containing suitable conventional coloring agents, flavoring agents, stabilizers and thickening agents. The inventive rifamycin derivatives of formula (I) can be used alone, or in conjunction with other antibacterial agents and/or non-antibacterial agents, as known to those skilled in the art.

Pharmaceutically acceptable refers to those properties and/or substances, which are acceptable from a pharmacological or toxicological point of view and from a physical or chemical point of view regarding composition, formulation, stability, patient acceptance, and bioavailability. Pharmaceutically acceptable hydrate means hydrates useful for administering the compounds of this invention, and suitable hydrates include the compounds complexed with at least one water molecule.

A pharmaceutically acceptable salt means a salt useful for administering compounds of the present invention. Suitable salts include acid addition salts when a basic group is present, such as occurs with a piperazinyl, or piperidinyl, or pyrrolidinyl group and the like, heteroaryls, such as imidazolyl, pyridinyl. Acid addition salts include those made from mineral acids, for example, hydrochloric, hydrobromic, hydroiodic, sulfuric, phosphoric, and the like, organic sulfonic acids, e.g., methanesulfonic, 2-hydroxyethyl sulfonates, organic carboxylic acids, e.g., amino and carbohydrate acids, e.g., gluconic, galacturonic, acetates, propionates, lactates, maleates, malates, succinates, tartrates, citric acid, fumarates, and the like. These salts can be in a hydrated form.

A pharmaceutically acceptable prodrug means a prodrug useful for administering the compounds of this invention, and metabolized in vivo to give pharmaceutically active forms of the inventive compounds of formula (I). Suitable prodrugs include acid derivatives, for example, amides, esters, for example, methyl esters, ethyl esters, and the like. These prodrugs also can be in a hydrated form.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective amount" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the does lethal to 50% of the population) and the $ED_{50}$ (the dose pharmacologically effective to 50% of the population). The dose ratio between toxic and therapeutic effects is the therapeutic index, which is expressed as the ratio between $LD_{50}$ and $ED_{50}$. Compounds exhibiting high therapeutic indices are preferred. The data obtained from such data can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

Humans and other mammals, for example, cattle, horses, sheep, hogs, dogs, and cats, can be treated with the inventive rifamycin derivatives (I) of the present invention. The rifamycin derivatives (I) of the present invention can be administered in a manner and in dosage forms similar to those of the known anti-bacterial agents described above. In therapeutic use for treating, or combating, bacterial infections in humans and warm-blooded animals, the compounds of formula (I), or pharmaceutical compositions thereof, are administered by conventional techniques, such as orally in solid and liquid dosage forms and/or parenterally (IV, IM, SC), at a unit dosage form to obtain and maintain a concentration, that is, an amount, or blood-level of active component in the animal undergoing treatment which is antibacterially effective or appropriate.

Generally, the amount of compound (I) in a pharmaceutical composition is about 0.5% to about 90% by weight. An antibacterially effective dosage of compound (I) is about 0.1 to about 100 mg/kg of body weight/day, more preferably about 3 to about 50 mg/kg of body weight/day. The quantity of the rifamycin derivatives of formula (I) in the pharmaceutical composition, the exact unit dosage form thereof to be administered, the frequency of administration, and the route of administration will vary, and can be adjusted widely depending upon a number of factors known to those skilled in the art including the particular route of administration, the particular compound being used, the potency of the particular compound, the desired concentration, the age, weight, sex, and general physical condition and requirements of the patient, the nature and severity of the bacterial infection being treated, and the like, as is well known to the physician treating infectious diseases. Also, it is to be understood that the initial dosage administered can be increased beyond the upper level in order to rapidly achieve the desired blood-level or the initial dosage can be smaller than the optimum and the daily dosage can be progressively increased during the course of treatment depending on the particular situation. The usual pharmaceutical dosage forms appropriate for parenteral (mixture, suspension in oil) and oral (tablet, capsule, syrup, suspension, etc) administration are known to those skilled in the art.

Compounds of the present invention can be administered by any suitable route, for example by oral, topical, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or infused together with an IV fluid, like 5% dextrose or normal saline.

If the compounds or pharmaceutical compositions of the present invention are administered parenterally, i.e., by injection, for example, by intravenous injection or by other parenteral routes of administration, it generally is as a soluble salt (acid addition salt or base salt) of the compound according to formula (I) in a pharmaceutically acceptable amount dissolved in a pharmaceutically acceptable liquid carrier such as, for example, water-for-injection, and a buffer to provide a suitable buffered isotonic solution, for example, having a pH of about 3.5 to about 10.

Suitable buffering agents include, for example, trisodium orthophosphate, sodium bicarbonate, sodium citrate, N-methylglucamine, L(+)-lysine, and L(+)-arginine. A compound of formula (I) generally is dissolved in the carrier in an amount sufficient to provide a pharmaceutically acceptable injectable concentration in the range of about 1 to about 400 mg/ml of solution. The resulting liquid pharmaceutical composition is administered so as to obtain the above-mentioned antibacterially effective amount of dosage.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5 to about 95% compound of the present invention, and preferably from about 25 to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5 to about 90% by weight of a compound of the present invention, and preferably about 1 to about 50% of a compound of the present invention.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention can be delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator-can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances, which increase the viscosity of the suspension. Optionally, the suspension also can contain suitable stabilizers or agents that increase the Solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

For topical administration, the present compounds can be applied in neat form, e.g., when the compound is a liquid. However, it is desirable to administer the compounds to the skin as compositions in combination with a dermatologically acceptable carrier, which can be a solid, semi-solid, or a liquid. Useful solid carriers include, but are not limited to, finely divided solids such as talc, clay, microcrystalline cellulose, silica, alumina, and the like. Useful liquid carriers include, but are not limited to, water, alcohols, glycols, and water-alcohol/glycol blends in which the present compounds can be dissolved or dispersed at effective levels, optionally with the aid of a surfactant. Adjuvants, such as fragrances and additional antimicrobial agents, can be added to optimize the properties for a given use. The resultant liquid compositions can be applied topically by absorbent pads, used to impregnate bandages and other dressings, or sprayed onto the affected area using pump-type or aerosol sprayers. For veterinary use, a compound of formula (I) or a nontoxic sale thereof, is administered as a suitably acceptable formulation in accordance with normal veterinary practice. The veterinarian can readily determine the dosing regimen and route of administration that is most appropriate for a particular animal.

EXAMPLES

General Materials And Procedures

All starting material used in these examples are either purchased from commercial sources or prepared according to published procedures. Reagents were purchased from commercial sources and used without further purification. All temperatures are in degrees Centigrade. When solvent pairs are used, the ratios of solvents used are volume/volume (v/v). When the solubility of a solid in a solvent is used the ratio of the solid to the solvent is weight/volume (wt/v). Reactions with moisture-sensitive reagents were performed under a nitrogen atmosphere. Concentration of solutions was performed by reduced pressure (in vacuo) rotary evaporation. Flash chromatography is performed using silica gel 60 as normal phase adsorbent or C18 silica gel as reverse phase adsorbent. Thin layer chromatography ("TLC") is performed using pre-coated plates purchased from E. Merck (Darmstadt, Germany) and spots are visualized with long-wave ultraviolet light followed by an appropriate staining reagent. Preparative thin-layer chromatography (TLC) was performed using EM silica gel (SG) 60 $F_{254}$ plates (20×20 cm, thickness 2 mm), bands are visualized with long-wave ultraviolet light lamp. Nuclear magnetic resonance ("NMR") spectra are recorded on a Varian 400 (Varian, Palo Alto, Calif.) MHz magnetic resonance spectrometer. $^1$H NMR refers to proton nuclear magnetic resonance spectroscopy with chemical shifts reported in ppm downfield from tetramethylsilane or using the residual solvent signal (CHCl$_3$=δ 7.27, CH$_3$OH=δ 3.31) as internal standard. $^1$H NMR information is tabulated in the following format: number of protons, multiplicity (s, singlet; d, doublet; t, triplet; q, quartet; m, multiplet; td, triplet of doublet; dt, doublet of triplet), coupling constant (s) (J) in hertz. The prefix app is occasionally applied in cases where the true signal multiplicity is unresolved and prefix br indicates a broad signal. Electrospray ionization mass spectra are recorded on a Finnegan LCQ advantage spectrometer (Thermoquest, San Jose, Calif.) and reported as M+H or M+Na, referring to protonated molecular ion or its sodium complex.

Abbreviations

Abbreviations as used herein have the meanings known by one skilled in the art. Specifically, Ac represents acetyl group, BOC represents t-butoxycarbonyl group, Bn represents benzyl group, Bu represents butyl group, Bz represents benzoyl group, Cbz represents benzyloxycarbonyl group, DCM represents dichloromethane, DMAP represents 4-N,N-dimethylaminopyridine, DMF represents N,N-dimethylformamide, DMSO represents dimethyl sulfoxide, Et represents ethyl group, EtOAc represents ethyl acetate, Me represents methyl group, Ph represents phenyl group, Pr represents propyl group, TEA represents triethylamine, TFA represents trifluoroacetic acid, THF represents tetrahydrofuran, and TMS is trimethylsilyl group. The following abbreviations are also used: millimole (mmol), milliliter (mL), milligram (mg), microliter (uL).

The following examples describe how to prepare the various compounds and/or perform the various processes of the invention, and are to be construed as merely illustrative, and not limitations of the preceding disclosure in any way whatsoever. Those skilled in the art will recognize appropriate variations from the procedures both as to reagents and as to reaction conditions and techniques.

Example 1

(R)-5'-[3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-yl]-3'-hydroxy-benzoxazinorifamycin:

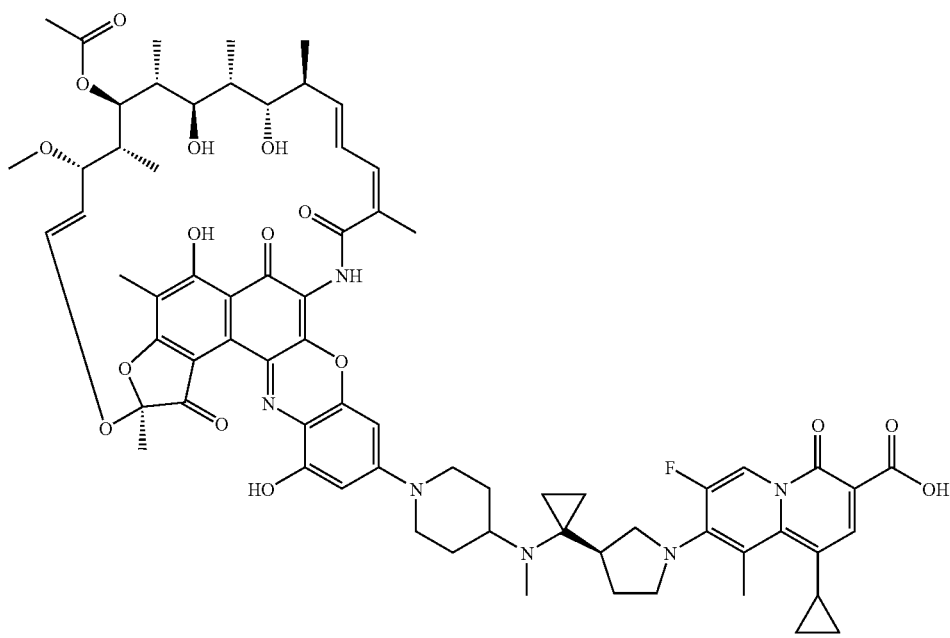

To a stirred solution of 3'-hydroxy-benzoxazinorifamycin (100.0 mg, 0.125 mmol) prepared according to the procedure described in Helv. Chim. Acta., in DMSO (3.0 mL), was added (R)-1-cyclopropyl-7-fluoro-9-methyl-8-[3-[1-(methyl-piperidin-4-yl-amino)-cyclopropyl]-pyrrolidin-1-yl]-4-oxo-4H-quinolizine-3-carboxylic acid (121 mg, 0.25 mmol)

prepared according to the procedure described in United States Patent Application Publication No. US2006/0019986 and manganese (IV) oxide (99.0 mg). The resulting mixture was allowed to stir at room temperature for one hour before the addition of triethylamine (60.7 mg, 0.6 mmol). The resulting mixture was allowed to stir at ambient temperature for 18 hours. Alter addition of dichloromethane to the reaction mixture, manganese dioxide was filtered off. The filtrate was washed successively with water and with saturated brine solution, and dried over anhydrous sodium sulfate. The solvent was removed under reduced pressure to give a dark-brown solid. The crude product is purified by preparative TLC (10% methanol/dichloromethane) to give the title compound as a dark-blue solid (17.2 mg).

ESI MS m/z 1281 (M+H$^+$); $^1$H NMR (400 MHz, CDCl$_3$) δ 13.85 (s, 1H), 10.01 (bs, 1H), 9.07 (d, J=10.1 Hz, 1H), 8.23 (s, 1H), 6.60 (d, J=11.0 Hz, 1H), 6.44 (s, 11H), 6.29 (s, 1H), 5.97 (bs, 1H), 5.72 (m, 2H), 5.16-4.56 (m, 2H), 4.05 (d, J=13.4 Hz, 1H), 3.62 (s, 2H), 3.06 (m, 2H), 2.90 (d, J=15.4 Hz, 1H), 2.73 (s, 1H), 2.59 (s, 3H), 2.39 (s, 3H), 2.26 (s, 3H), 2.14 (m, 4H), 1.78 (s, 1H), 1.25 (m, 2H), 1.17 (m, 2H), 0.90 (d, J=7.4 Hz, 3H), 0.78 (d, J=5.3 Hz, 2H), 0.70 (d, J=6.1H, 3H), 0.61 (d, J=4.6 Hz, 2H), 0.49 (m, 2H), −0.11 (d, J=7.3 Hz, 3H), −0.21 (d, J=7.011z, 3H).

Example 2

(R)-5'-[4-[1-[1-(3-Carboxy-1-cyclopropyl-6-fluoro-8-methoxy-4-oxo-1,4-dihydro-quinoline-7-yl)-pyrrolidin-3-yl-cyclopropyl-methyl]-amino]-piperidin-1-yl]-3'-hydroxy-benzoxazinorifamycin:

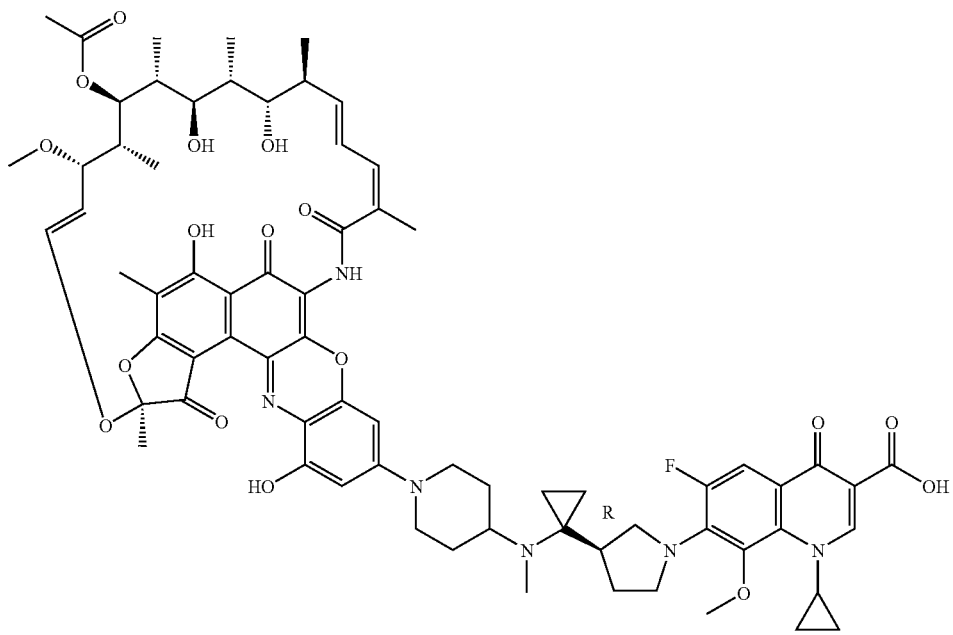

To a stirred solution of 3'-Hydroxybenzoxazinorifamycin (0.5 g, 0.6 mmol) prepared according to the procedure described in Helv. Chim. Acta., 1973, 56, p2369, and 1-cyclopropyl-6-fluoro-8-methoxy-7-{3-[1-(methyl-piperidin-4-yl-amino)-cyclopropyl]-pyrrolidin-1-yl}-4-oxo-1,4-dihydro-quinoline-3-carboxylic acid (0.5 g, 1.0 mmol) prepared according to the procedure described in a published United States patent application No. US20050261262, in DMSO (5 ml) was added Et3N (0.14 ml, 1.0 mmol) followed by MnO$_2$ (0.48 g, 5.52 mmol). The mixture was stirred at 23° C. for 4 days. The mixture was filtered then diluted with water and extracted with EtOAc (2×100 ml) to give a blue solution. The solution was dried over Na2SO4 and concentrated in vacuo to give a blue residue. The product was purified by preparative thin layer chromatography to give the title compound as a blue solid (35 mg).

$^1$H NMR (400 MHz, CDCl$_3$) δ9.99-9.95 (broad s, 1H), 8.72 (s, 1H), 7.76 (d, J=12.9 Hz, 1H), 6.41 (s, 1H), 6.30-6.20 (br s, 1H), 4.98-4.92 (m, 2H), 3.99-3.86 (m, 4H), 3.82-3.72 (m, 1H), 3.44 (s, 3H), 3.44-3.34 (m, 3H), 3.21-2.91 (m, 5H), 2.90-2.82 (m, 1H), 2.62-2.45 (m, 1H), 2.39 (s, 3H), 2.22 (s, 3H), 2.01 (s, 3H), 2.01-1.83 (m, 4H), 1.68-1.62 (m, 3H), 1.62-1.23 (m, 14H), 1.24-1.12 (s, 3H), 1.18-0.94 (m, 5H), 0.95-0.51 (m, 18H); ESI MS1297 (M+H).

Example 3

5'-[4-(3-Carboxy-1-cyclopropyl-6-fluoro-8-methoxy-4-oxo-1,4-dihydroquinolin-7-yl)-piperazin-1-yl]-3'-hydroxy-benzoxazinorifamycin:

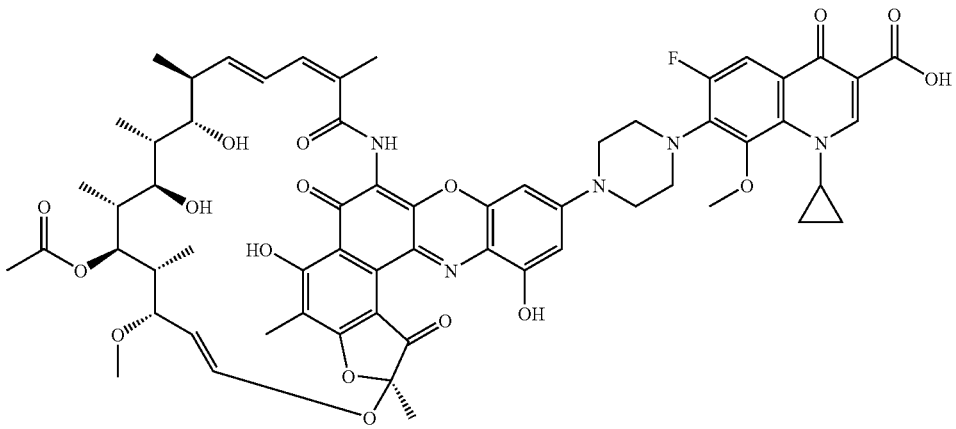

The title compound was prepared by using the same procedure as described for the preparation of Example 1 except 1-cyclopropyl-6-fluoro-8-methoxy-7-(piperazin-1-yl)-4-oxo-1,4-dihydro-quinoline-3-carboxylic acid was used in place of (R)-1-cyclopropyl-7-fluoro-9-methyl-8-[3-[1-(methyl-piperidin-4-yl-amino)-cyclopropyl]-pyrrolidin-1-yl]-4-oxo-4H-quinolizine-3-carboxylic acid. The title compound was isolated as blue solid. ESI MS m/z 1160 (M+H$^+$); $^1$H NMR (400 MHz, CDCl$_3$) δ 10.00 (s, 1H), 8.83 (s, 1H), 7.92 (d, J=11.9 Hz, 1H), 6.51 (s, 1H), 6.37 (s, 1H), 5.99 (bs, 1H), 5.98 (dd, J=7.7 Hz, 11.7 Hz, 1H), 4.02 (m, 1H), 3.79 (s, 3H), 3.68 (br m, 4H), 3.57 (br m, 4H), 3.39 (m, 1H), 3.04 (m, 4H), 2.27 (s, 3H), 2.11 (s, 3H), 2.01 (s, 3H), 1.77 (s, 2H), 1.23 (d, J=7.8 Hz, 3H), 1.01 (d, J=4.1 Hz, 3H), 0.91 (d, J=3.9 Hz, 3H), 0.76 (m, 3H).

Example 4

5'-[4-[1-(3-Carboxy-1-cyclopropyl-6-fluoro-8-methoxy-4-oxo-1,4-dihydro-quinoline-7-yl)-piperidin-4-yl-amino]-piperidin-1-yl]-3'-hydroxy-benzoxazinorifamycin:

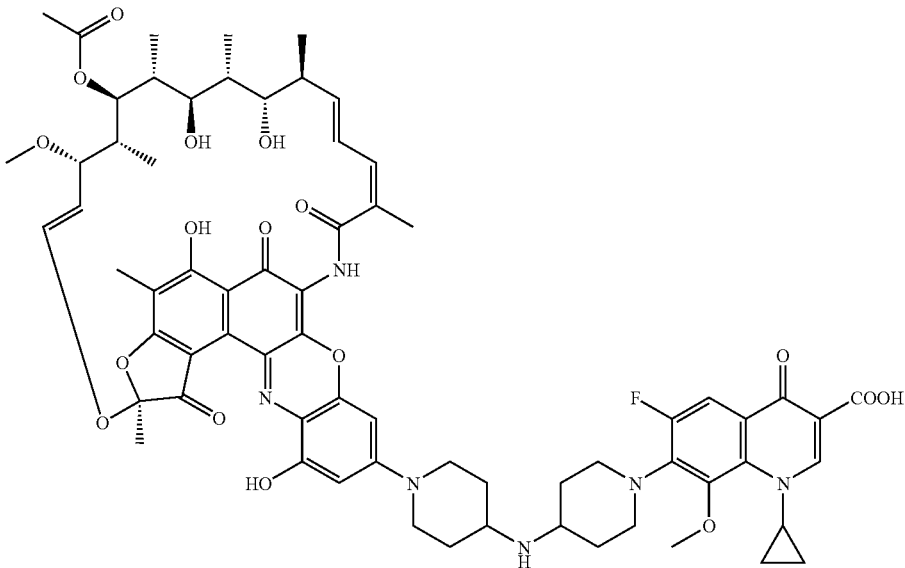

Step 1: 4-(Piperidin-4-ylamino)-piperidine-1-carboxylic acid tert-butyl ester. To a solution of 4-(1-benzyl-piperidin-4-ylamino)-piperidine-1-carboxylic acid tert-butyl ester (1.51 g) in 20 mL acetic acid was added 0.23 g 10% palladium on carbon, the resulting suspension was shaken under hydrogen (50 psi) in Parr shaker apparatus for 12 hours. The suspension was filtered through a layer of celite and the solvent was removed under vacuum. To the residue was added 10% aq. NaOH and extracted with dichloromethane (2×). The combined organic layers were washed with saturated brine and dried over anhydrous sodium sulfate. The title compound was obtained as clear syrup (1.16 g). ESI MS m/z 284 (M+H$^+$); $^1$H NMR (400 MHz, CDCl$_3$) δ 4.00 (m, 2H), 3.06 (d, J=10.1 Hz, 2H), 2.74 (m, 4H), 2.57 (t, J=10.1 Hz, 2H), 1.81 (t, J=14.1 Hz, 1H), 1.42 (s, 9H), 1.17 (m, 4H).

Step 2: 7-[4-(1-tert-Butoxycarbonyl-piperidin-4-ylamino)-piperidin-1-yl]-1-cyclopropyl-6fluoro-8-methoxy-4-oxo-1,4-dihydro-quinoline-3-carboxylic acid. To a stirred solution of 1-cyclopropyl-6,7-difluoro-8-methoxy-4-oxo-1,4-dihydro-quinoline-3-carboxylic acid (295 mg, 1.0 mmol) in acetonitrile (5 mL) was added 4-(piperidin-4-ylamino)-piperidine-1-carboxylic acid tert-butyl ester (339 mg, 1.2 mmol) followed by the addition of 8-diazabicyclo[5.4.0]undec-7-ene (DBU, 182 mg, 1.2 mmol). The resulting stirred solution was then heated in a 60-65° C. oil bath for two days. The cooled reaction mixture was filtered through a fritted funnel. The filtrate was condensed to dryness. Dichloromethane was added into this residue and washed with water twice. The resulting organic layer was washed one more time with saturated brine and dried over sodium sulfate. The solvent was removed under reduced pressure to give crude material as light brown syrup. This crude product was further purified with 10% methanol in dichloromethane by preparative TLC plate to afford pure title product as yellow solid (100 mg). ESI MS m/z 559 (M+H$^+$); $^1$H NMR (400 MHz, CDCl$_3$) δ 8.73 (s, 1H), 7.76 (d, J=12.4 Hz, 1H), 3.98 (m, 3H), 3.71 (s, 3H), 3.51 (d, J=12.1 Hz, 2H), 3.17 (t, J=12.3 Hz, 2H), 2.76 (br s, 1H), 1.92 (d, J=11.8 Hz, 2H), 1.83 (d, J=11.6 Hz, 2H), 1.49 (q, J=8.6 Hz, 2H), 1.38 (s, 9H), 1.20 (q, J=7.9 Hz, 2H), 1.15 (d, J=7.1 Hz, 2H), 0.94 (d, J=5.6 Hz, 2H).

Step 3: 1-Cyclopropyl-6-fluoro-8-methoxy-4-oxo-7-[4-(piperidin-4-ylamino)-piperidin-1-yl]-1,4-dihydro-quinoline-3-carboxylic acid. To a stirred solution of 7-[4-(1-tert-Butoxycarbonyl-piperidin-4-ylamino)-piperidin-1-yl]-1-cyclopropyl-6-fluoro-8-methoxy-4-oxo-1,4-dihydro-quinoline-3-carboxylic acid (113 mg, 0.2 mmol) in dichloroethane (1.5 mL) was added trifluoroacetic acid (692 mg, 6.07 mmol). The resulting mixture was stirred for 3 hours before condensed to dryness. To this residue was added saturated aqueous sodium carbonate followed by the addition of acetic acid to pH around 6. This aqueous solution was extracted with 20% (v/v) isopropanol/dichloromethane. The combined organic layers were dried over sodium sulfate and condensed to give product as slightly yellow syrup, which was used directly for next reaction. ESI MS m/z 459 (M+H$^+$); $^1$H NMR (400 MHz, CDCl$_3$) δ 8.74 (s, 1H), 7.78 (d, J=11.6 Hz, 1H), 3.98 (m, 3H), 3.71 (s, 3H), 3.54 (d, J=13.2 Hz, 2H), 3.33 (t, J=13.3 Hz, 2H), 3.14 (m, 1H), 2.91 (d, J=12.5 Hz, 2H), 2.11 (d, J=11.7 Hz, 2H), 2.00 (m, 2H), 1.78 (m, 4H), 1.16 (d, J=7.0 Hz, 2H), 0.93 (d, J=3.3 Hz, 2H).

Step 4: 5'-[4-[1-(3-Carboxy-1-cyclopropyl-6-fluoro-8-methoxy-4-oxo-1,4-dihydro-quinoline-7-yl)-piperidin-4-yl-amino]-piperidin-1-yl]-3'-hydroxy-benzoxazinorifamycin. The title compound was prepared by using the same procedure as described for the preparation of Example 1 except 1-cyclopropyl-6-fluoro-8-methoxy-4-oxo-7-[4-(piperidin-4-ylamino)-piperidin-1-yl]-1,4-dihydro-quinoline-3-carboxylic acid was used in place of (R)-1-cyclopropyl-7-fluoro-9-methyl-8-[3-[1-(methyl-piperidin-4-yl-amino)-cyclopropyl]-pyrrolidin-1-yl]-4-oxo-4H-quinolizine-3-carboxylic acid. The title compound was isolated as blue solid. ESI MS m/z 1257 (M+H$^+$); $^1$H NMR (400 MHz, CDCl$_3$) δ 10.00 (br s, 1H), 8.79 (s, 1H), 7.83 (d, J=12.8 Hz, 1H), 6.45 (s, 1H), 6.30 (s, 1H), 5.98 (bs, 1H), 4.98 (m, 1H), 4.00 (m, 3H), 3.79 (s, 3H), 3.53 (br m, 2H), 3.15-3.00 (m, 5H), 2.27 (s, 3H), 2.09 (s, 3H), 2.01 (s, 3H), 1.76 (s, 2H), 1.19 (d, J=6.1 Hz, 3H), 1.07-0.62 (complex pattern 9H).

Example 5

(R/S)-5'-[4-[[1-(1-Cyclopropyl-6-fluoro-8-methoxy-4-oxo-1,4-dihydro-quinolin-7-yl)-pyrrolidin-3-ylmethyl]-(2-dimethylamino-ethyl)-amino]-piperidin-1-yl]-3'-hydroxy-benzoxazinorifamycin:

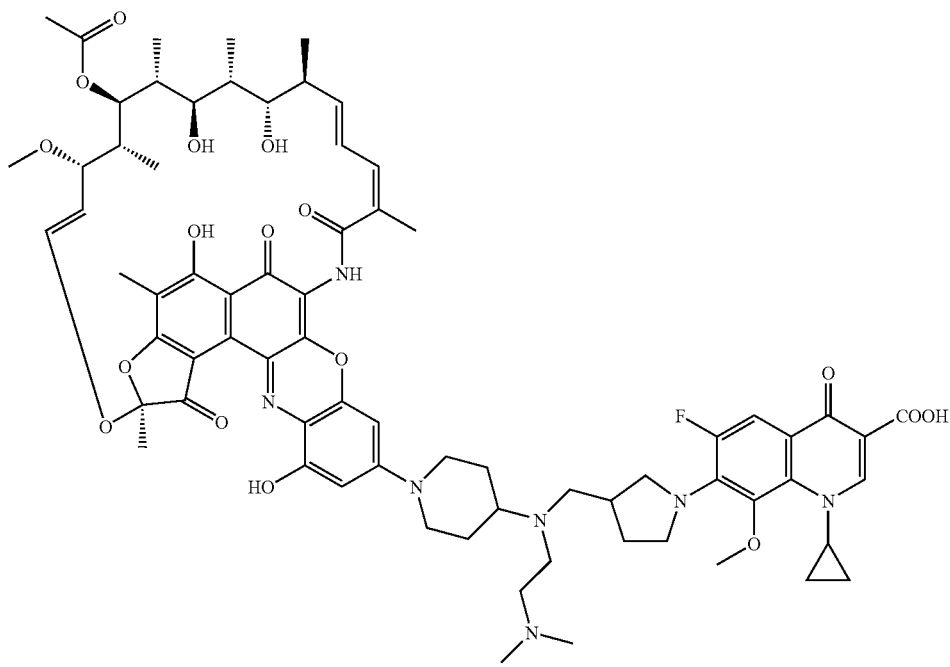

Step 1: 4-[(2-Dimethylamino-ethyl)-pyrrolidin-3-ylmethyl-amino]-piperidine-1-carboxylic acid tert-butyl ester. The title compound was prepared by using the same procedure as described for the preparation of 4-(piperidin-4-ylamino)-piperidine-1-carboxylic acid tert-butyl ester in Example 4, Step 1 except 4-[(1-benzyloxycarbonyl-pyrrolidin-3-ylmethyl)-(2-dimethylamino-ethyl)-amino]-piperidine-1-carboxylic acid tert-butyl ester was used in place of 4-(1-benzyl-piperidin-4-ylamino)-piperidine-1-carboxylic acid tert-butyl ester. The title compound was obtained as light brown syrup. ESI MS m/z 355 (M+H$^+$); $^1$H NMR (400 MHz, CDCl$_3$) δ 4.15 (br s, 1H), 2.98 (d, J=7.5 Hz, 10.9 Hz, 1H), 2.90 (q, J=7.2 Hz, 1H), 2.71-2.50 (m, 6H), 2.40 (q, J=4.9 Hz, 1H), 2.31 (m, 3H), 2.22 (s, 3H), 2.20 (s, 3H), 1.87-1.59 (m, 8H), 1.44 (s, 9H), 1.35 (m 2H).

Step 2: 7-(3-{[(1-tert-Butoxycarbonyl-piperidin-4-yl)-(2-dimethylamino-ethyl)-amino]-methyl}-pyrrolidin-1-yl)-1-cyclopropyl-6-fluoro-8-methoxy-4-oxo-1,4-dihydro-quinoline-3-carboxylic acid. The title compound was prepared by using the same procedure as described for the preparation of 7-[4-(1-tert-butoxycarbonyl-piperidin-4-ylamino)-piperidin-1-yl]-1-cyclopropyl-6-fluoro-8-methoxy-4-oxo-1,4-dihydro-quinoline-3-carboxylic acid in Example 4, Step 2 except 4-[(2-dimethylamino-ethyl)-pyrrolidin-3-ylmethyl-amino]-piperidine-1-carboxylic acid tert-butyl ester was used in place of 4-(piperidin-4-ylamino)-piperidine-1-carboxylic acid tert-butyl ester. The title compound was obtained as light brown foaming solid. ESI MS m/z 630 (M+H$^+$); $^1$H NMR (400 MHz, CDCl$_3$) δ 8.74 (s, 1H), 7.76 (d, J=14.1 Hz, 1H), 3.96 (m, 1H), 3.66 (m, 4H), 3.50 (s, 3H), 3.40 (m, 2H), 2.78-2.23 (complex pattern, 8H), 2.20 (s, 3H), 2.18 (s, 3H), 2.07 (m, 1H), 1.93-1.52 (complex pattern, 8H), 1.42 (s, 9H), 1.14 (m, 2H), 0.97 (m, 2H).

Step 3: 1-Cyclopropyl-7-(3-{[(2-dimethylamino-ethyl)-piperidin-4-yl-amino]-methyl }-pyrrolidin-1-yl)-6-fluoro-8-methoxy-4-oxo-1,4-dihydro-quinoline-3-carboxylic acid. The title compound was prepared by using the same procedure as described for the preparation of 1-cyclopropyl-6-fluoro-8-methoxy-4-oxo-7-[4-(piperidin-4-ylamino)-piperidin-1-yl]-1,4-dihydro-quinoline-3-carboxylic acid in Example 4, Step 3 except 7-(3-{[(1-tert-butoxycarbonyl-piperidin-4-yl)-(2-dimethylamino-ethyl)-amino]-methyl}-pyrrolidin-1-yl)-1-cyclopropyl-6-fluoro-8-methoxy-4-oxo-1,4-dihydro-quinoline-3-carboxylic acid was used in place of 7-[4-(1-tert-butoxycarbonyl-piperidin-4-ylamino)-piperidin-1-yl]-1-cyclopropyl-6-fluoro-8-methoxy-4-oxo-1,4-dihydro-quinoline-3-carboxylic acid. The title compound was obtained as light yellow oil. ESI MS m/z 459 (M+H$^+$); $^1$H NMR (400 MHz, CDCl$_3$) δ 8.71 (s, 1H), 7.46 (d, J=14.2 Hz, 1H), 4.11 (br s, 1H), 3.70 (m, 1H), 3.57 (m, 1H), 3.54 (s, 3H), 3.46 (m, 4H), 2.99 (m, 4H), 2.88 (m, 2H), 2.71 (s, 6H), 2.52 (m, 1H), 2.12 (q, J=5.5 Hz, 1H), 2.00 (dd, J=12.7 Hz, 19.4 Hz, 2H), 1.78 (q, J=11.6 Hz, 2H), 1.71 (q, J=8.4 Hz, 2H), 1.24 (m, 2H), 1.09-0.95 (m, 4H).

Step 4: (R/S)-5'-[4-[[1-(1-Cyclopropyl-6-fluoro-8-methoxy-4-oxo-1,4-dihydro-quinolin-7-yl)-pyrrolidin-3-ylmethyl]-(2-dimethylamino-ethyl)-amino]-piperidin-1-yl]-3'-hydroxy-benzoxazinorifamycin. The title compound was prepared by using the same procedure as described for the preparation of Example 1 except 1-cyclopropyl-7-(3-{[(2-dimethylamino-ethyl)-piperidin-4-yl-amino]-methyl}-pyrrolidin-1-yl)-6-fluoro-8-methoxy-4-oxo-1,4-dihydro-quinoline-3-carboxylic acid was used in place of (R)-1-cyclopropyl-7-fluoro-9-methyl-8-[3-[1-(methyl-piperidin-4-yl-amino)-cyclopropyl]-pyrrolidin-1-yl]-4-oxo-4H-quinolizine-3-carboxylic acid. The title compound was isolated as blue solid. ESI MS m/z 1327 (M+H$^+$); $^1$H NMR (400 MHz, CDCl$_3$) δ 9.92 (br s, 1H), 8.74 (s, 1H), 7.74 (d, J=13.9 Hz, 1H), 6.38 (s, 1H), 6.26 (s, 1H), 6.08 (br s, 1H), 4.95 (m, 1H), 4.06 (m, 2H), 3.96 (s, 1H), 3.68 (q, J=5.7 Hz, 2H), 3.59 (m, 1H), 3.50 (s, 3H), 3.39 (s, 1H), 3.00 (m, 4H), 2.86 (m, 1H), 2.69 (s, 1H), 2.61-2.14 (complex pattern), 2.09 (br s, 4H), 1.99 (br s, 4H), 1.93-1.26 (complex pattern), 1.17 (m, 4H), 0.98 (m, 3H), 0.89 (m, 6H), 0.74 (br s 3H).

Example 6

4-Deoxy-3,4-[2-spiro-[1-(3-carboxy-1-cyclopropyl-6-fluoro-4-oxo-1,4-dihydroquinolin-7-yl)-piperidin-4-yl]]-(1H)-imidazo-(2,5-dihydro)rifamycin S:

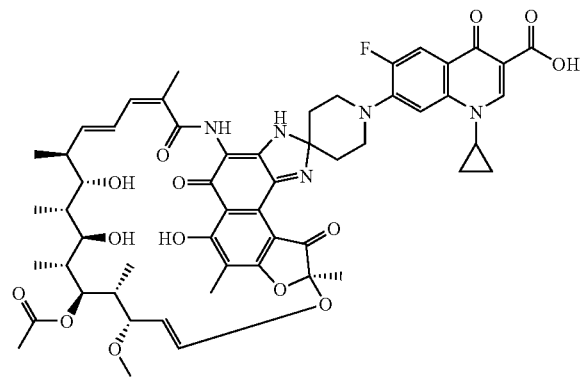

To a stirred solution of 1-cyclopropyl-6-fluoro-4-oxo-7-(4-oxo-piperidin-1-yl)-1,4-dihydro-quinoline-3-carboxylic acid (45 mg, 0.13 mmol), prepared according to a procedure described in a literature (Radl, S.; Kovarova, L.; Collect. Czech. Chem. Commun. 56, 1991, 2406-2412), in THF was added ammonium acetate (80 mg, 1.04 mmol) and heated for 10 min and cooled to room temperature, followed by the addition of Zn (8 mg, 0.13 mmol) and 3-amino-4-deoxy-4-imino-rifamycin S (138 mg, 0.19 mmol), prepared by following a literature report (U.S. Pat. No. 4,017,481), and the resulting reaction mixture was stirred overnight at room temperature. The mixture was diluted with ethyl acetate and washed with water and saturated brine. The organic layer was dried over anhydrous Na$_2$SO$_4$, filtered and evaporated. The residue was purified by silica gel column chromatography (7% MeOH in CH$_2$Cl$_2$) to give the title product (10 mg) as purple solid.

ESI MS m/z 1036 (M+H$^+$); $^1$H NMR (400 MHz, CDCl$_3$) δ 15.04 (s, 1H), 14.56 (s, 1H), 8.95 (s, 1H), 8.81 (s, 1H), 8.25 (s, 1H), 8.07 (d, J=13.2 Hz, 1H), 7.51 (d, J=7.2 Hz, 1H), 6.41 (dd, J=15.6 Hz and 10.2 Hz, 1H), 6.29 (d, J=10.4 Hz, 1H), 6.16 (d, J=12.8 Hz, 1H), 6.00 (dd, J=15.6 Hz and 6.8 Hz, 1H), 5.12 (dd, J=12.8 Hz and 6.4 Hz, 1H), 4.74 (d, J=10.4 Hz, 1H), 3.92-3.84 (m, 4H), 3.75-3.66 (m, 2H), 3.59 (br d, J=6.4 Hz, 2H), 3.32-3.30 (m, 1H), 3.08 (s, 3H), 3.03-2.99 (m, 1H), 2.44-2.38 (m, 3H), 2.35 (s, 3H), 2.05 (s, 3H), 2.01 (s, 3H), 1.83-1.67 (m, 3H), 1.74 (s, 3H), 1.46-1.40 (m, 3H), 1.29-1.24 (m, 3H), 1.04 (d, J=6.8 Hz, 3H), 0.84 (d, J=6.8 Hz, 3H), 0.63 (d, J=6.8 Hz, 3H), −0.03 (d, J=6.8 Hz, 3H).

Example 7

4-Deoxy-3,4-[2-spiro-[1-(3-carboxy-1-cyclopropyl-6-fluoro-8-methoxy-4-oxo-1,4-dihydroquinolin-7-yl)-piperidin-4-yl]]-(1H)-imidazo-(2,5-dihydro)rifamycin S:

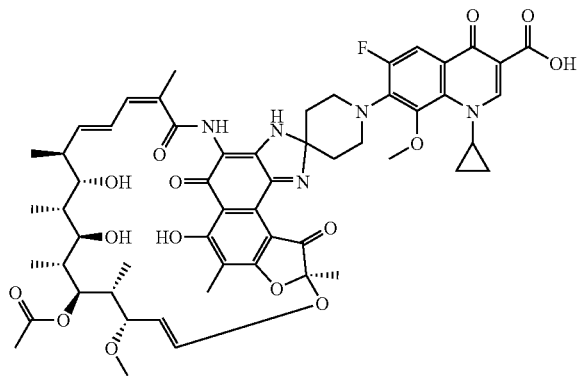

Step 1: 1-cyclopropyl-6-fluoro-8-methoxy-4-oxo-7-(4-oxo-piperidin-1-yl)-1,4-dihydro-quinoline-3-carboxylic acid. To a stirred solution of 1-cyclopropyl-6,7-difluoro-8-methoxy-4-oxo-1,4-dihydro-quinoline-3-carboxylic acid borate complex (0.67 mg, 1.6 mmol, prepared as described in EP 0464823) was added 1,4-dioxa-8-aza-spiro[4.5]decane (0.44 g, 1.80 mmol), triethyl amine (0.44 ml, 3.2 mmol) and acetonitrile (10 ml). The mixture was stirred at 23° C. for 12 hours and then heated at reflux for 3 hours. The mixture was cooled and water (20 ml) was added and the mixture heated to reflux for 4 hours. The organic solvent was removed in vacuo and the product was isolated by filtration. The solid (0.87 g) was added to a 1:2 mixture of ethanol:water (v/v, 30 ml) and p-toluenesulfonic acid (34 mg, 0.18 mmol) was added. The mixture was heated to reflux for 24 h then cooled and concentrated. The precipitated product was isolated by filtration to give 480 mg (68%) of the title product as a tan solid. $^1$H NMR (CDCl$_3$) δ 8.84 (s, 1H), 7.93 (d, J=11.6 Hz, 1H), 4.04-4.09 (m, 1H), 3.81 (s, 3H), 3.69-3.72 (m, 2H), 2.65-2.67 (m, 2H), 1.23-1.28 (m, 2H), 1.02-1.03 (m, 2H); ESI MS 374 (M+H).

Step 2: 4-Deoxy-3,4-[2-spiro-[1-(3-carboxy-1-cyclopropyl-6-fluoro-8-methoxy-4-oxo-1,4-dihydroquinolin-7-yl)-piperidin-4-yl]]-(1H)-imidazo-(2,5-dihydro)rifamycin S. The title compound was prepared by using the same procedure as described for the preparation of Example 6 except 1-cyclopropyl-6-fluoro-8-methoxy-4-oxo-7-(4-oxo-piperidin-1-yl)-1,4-dihydro-quinoline-3-carboxylic acid was used in place of 1-cyclopropyl-6-fluoro-4-oxo-7-(4-oxo-piperidin-1-yl)-1,4-dihydro-quinoline-3-carboxylic acid. The title compound was isolated as a purple solid. $^1$H NMR (CDCl$_3$) δ 9.03 (s, 1H), 8.90 (s, 1H), 8.41 (s, 1H), 7.98 (d, J=12 Hz, 1H), 6.44-6.47 (m, 1H), 6.33 (d, J=16 Hz, 1H), 6.20 (d, J=12.8 Hz, 1H), 6.07 (dd, J=6, 7.8 Hz, 1H), 5.16-5.20 (m, 1H), 4.82-4.84 (m, 1H), 4.09.4.16 (m, 2H), 3.98 (s, 3H), 3.69-3.76 (m, 2H), 3.38-3.96 (m, 1H), 3.12 (s, 3H), 3.0-3.13 (m, 1H), 2.27-2.39 (m, 3H), 2.39 (s, 3H), 2.09 (s, 3H), 2.10 (s, 3H), 2.11 (s, 3H), 1.80 (s, 3H), 1.64-1.83 (m, 6H), 1.59-1.44 (m, 2H), 1.10-1.58 (m, 4H), 1.09 (d, J=7.2 Hz, 3H), 0.89 (d, J=7.2 Hz, 3H), 0.66 (d, J=7.2 Hz, 3H), 0.009 (d, J=7.2 Hz, 3H); ESI MS m/z 1066 (M+H$^+$).

Example 8

(R/S)-4-Deoxy-3,4-[2-spiro-[1-[1-(3-carboxy-1-cyclopropyl-6-fluoro-8-methoxy-4-oxo-1,4-dihydroquinolin-7-yl)-pyrrolidin-3-methyl]-piperidin-4-yl]]-(1H)-imidazo-(2,5-dihydro)rifamycin S:

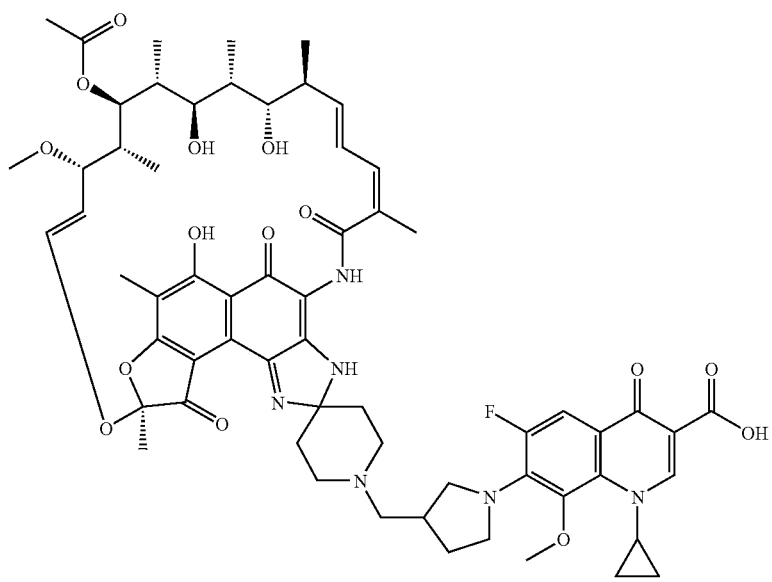

The title compound is prepared by using the same procedure as described for the preparation of Example 6 except 1-cyclopropyl-6-fluoro-8-methoxy-4-oxo-7-[3-(4-oxo-piperidin-1-ylmethyl)-pyrrolidin-1-yl]-,4-dihydro-quinoline-3-carboxylic acid is used in place of 1-cyclopropyl-6-fluoro-4-oxo-7-(4-oxo-piperidin-1-yl)-1,4-dihydro-quinoline-3-carboxylic acid. The title compound is isolated as a purple solid. ESI MS m/z 1149 (M+H$^+$).

Example 9

Biological Activity

As shown in Table 1 below, the compounds of Example 1, 2 and 3 demonstrated a potent antibacterial activity.

TABLE 1

Antibacterial Activity of Selected Examples against Wild-type and Genetically-Defined Resistant Strains of Bacteria

| | MIC (ug/mL) | | | | |
|---|---|---|---|---|---|
| Compound | S. aureus ATCC# 29213 | S. aureus rpoB$^{H481Y}$ | S. aureus gyrA$^{S84L}$ parC$^{S80F}$ | S. aureus rpoB$^{H481Y}$ gyrA$^{S84L}$ parC$^{S80F}$ | E. coli ATCC# 25922 |
| rifampin | 0.008 | >64 | 0.008 | >64 | 8 |
| ciprofloxacin | 0.24 | 0.24 | >32 | >32 | 0.008 |
| Example 1 | <0.004 | 0.12 | <0.004 | 2 | 0.5 |
| Example 2 | 0.008 | 0.5 | 0.016 | 4 | 4 |
| Example 3 | 0.008 | 0.24 | 0.008 | 8 | 4 |

Representative compounds are assayed for antimicrobial activity as follows: Minimum Inhibitory Concentrations (MICs) against *Staphylococcus aureus* ATCC 29213, its isogenic derivative, and *Escherichia coli* ATCC 25922 were determined by the microbroth dilution method, as per NCCLS guidelines (National Committee for Clinical Laboratory Standards 2000). The antimicrobial activity of the example compounds of the current invention and the reference compounds, rifampin and ciprofloxacin, are shown in Table 1. The inventive compounds display excellent activity against Gram-positive species, for example, *Staphylococcus aureus* ATCC 29213, and good activities against Gram-negatives, for example, *Escherichia coli* ATCC 25922. It is to be noted that the inventive compounds exhibit good activity against both genetically-defined rifamycin-resistant strains of *Staphylococcus aureus* (rpoB$^{H481Y}$), through genetic mutation in RNA polymerase, and quinolone-resistant strains of *Staphylococcus aureus* (gyrA$^{S84L}$ parC$^{S80F}$), through genetic mutations in gyrase and topoisomerase IV, while rifampin and ciprofloxacin are not as effective respectively consistent with their high MICs. The noted MIC up-shifts from both rifamycin-resistant (rpoB$^{H481Y}$) and quinolone-resistant (gyrA$^{S84L}$ parC$^{S80F}$) strains to a genetically-defined triple mutant strain (rpoB$^{H481Y}$, gyrA$^{S84L}$ parC$^{S80F}$) conferring resistance to both rifamycin and quinolone are consistent with the triple targeting nature of the inventive compounds. The residual activity of all three examples against the triple mutant *Staphylococcus aureus* (rpoB$^{H481Y}$, gyrA$^{S84L}$ parC$^{S80F}$) shown in Table 1 is not expected from a simple combination of rifampin and ciprofloxacin, with which activity would not have been expected.

The present compounds are surprisingly effective against a number of human and veterinary aerobic and anaerobic Gram positive, Gram negative pathogens, including the Staphylococci, for example *S. aureus*; Enterococci, for example *E. faecalis*; Streptococci, for example *S. pneumoniae*; Haemophilis, for example *H. influenza*; *Moraxella*, for example *M. catarrhalis*; and *Escherichia* for example *E. coli*; Mycobacteria, for example *M. tuberculosis; Helicobacter*, for example *H. pylori*; *Clostridium*, for example *C. difficile*; *Bacteroides* for example, *B. fragilis, B. vulgates*; intercellular microbes, for example *Chlamydia* and *Rickettsiae*; and *Mycoplasma*, for example *M. pneumoniae*, amongst others.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES CITED

U.S. Patent Documents

U.S. Pat. No. 4,219,478
U.S. Pat. No. 4,563,459
U.S. Pat. No. 4,620,007
U.S. Pat. No. 4,983,602
U.S. Pat. No. 5,880,283
U.S. Patent Application Publication No. US2005/0209210
U.S. Patent Application Publication No. US2005/0261262
U.S. Patent Application Publication No. US2006/0019985
U.S. Patent Application Publication No. US2006/0019986

OTHER PUBLICATIONS

Farr, B. M., Rifamycins, in *Principles and Practice of Infectious Diseases*, Mandell, G. L., Bennett, J. E., Dolin, R., Eds.; Churchhill Livingstone: Philadelphia; p. 348-361.

Greene, T. H. and P. G. M. Wuts, *Protective Groups in Organic Synthesis*, 2nd edition, John Wiley & Sons, New York, 1991.

Helv. Chim. Acta., 1973, 56, p. 2369.

Karchmer, A. W. et al: "Rifampin treatment of Prosthetic Valve Endocarditis Due to Staphylococcus epidermidis" Rev. Infect. Dis. 5 (S3): p. S543-548 (1983).

Kaufman C. A. et al: "Increasing resistance of *Staphylococcus aureus* to ciprofloxacin" Antimicrob Agents Chemother. 1990 Sep. 34(9):1862-3.

National Committee for Clinical Laboratory Standards, Methods for dilution antimicrobial susceptibility tests for bacteria that grow aerobically, 5th ed. M7A5. National Committee for Clinical Laboratory Standards, Wayne, Pa. 2000.

Watanakunakorn, C, "Interaction of Vancomycin and Rifampin Against *Staphyloccocus aureus*," Antimicrob. Agents & Chemother, 19(6): p. 1089-1091 (1981).

Yajko, D. M. et al: "In Vitro Susceptibility of *Mycobacterium avium* Complex to the New Fluoroquinolone Sparfloxacin and Comparison with Ciprofloxacin" Antimicrob. Agents & Chemother. 34(12): p. 2442-2444 (1990).

What is claimed is:
1. A compound of structural formula (I):

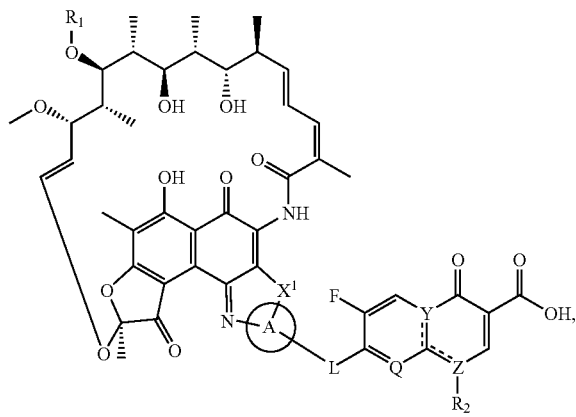

or a pharmaceutically acceptable salt thereof,
wherein:

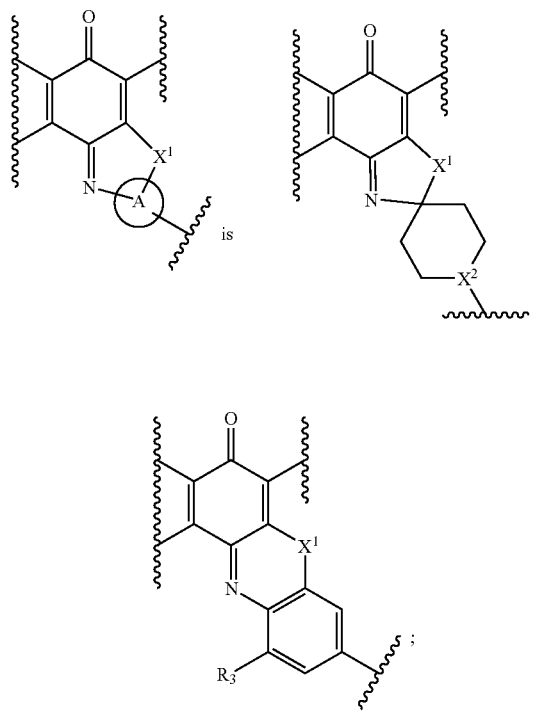

$X^1$ is $NH$, $NR_4$, O or S;
$X^2$ is N or $CR_5$;
L is a bond, or a linker group selected from one or a combination of two to three of the following groups:
1) $(C_1-C_6)$alkylene,
2) $(C_3-C_8)$cycloalkylene,
3) arylene,
4) heteroarylene,
5) heterocycloalkylene containing 1 to 3 heteroatoms,
6) —C(=O)—,
7) —C(=N—O—$R_6$)—,
8) —C=N—,
9) —O—,
10) —S(O)$_n$—, wherein n is number between 0 and 2,
11) —N($R_7$)—,
wherein the carbon or nitrogen atoms of the linker "L" group are optionally substituted by 1 to 3 substituents selected from $(C_1-C_6)$alkyl, substituted $(C_1-C_6)$alkyl, amino, $(C_1-C_6)$alkylamino, di$(C_1-C_6)$alkylamino, hydroxyl, $(C_1-C_6)$alkoxy, and heterocycloalkyl group;

Q is N or $CR_8$;
Y and Z are independently selected from C or N;
$R_1$ is H or acetyl group;
$R_2$, $R_4$, $R_5$, $R_6$, $R_7$ are independently a group selected from hydrogen, $(C_1-C_6)$alkyl, $(C_3-C_7)$cycloalkyl, aryl, heteroaryl, and heterocycloalkyl groups that are all optionally substituted;
$R_3$ is H, —OH or —SH; and
$R_8$ is H, F, Cl, CN, $CH_3$, '$OCH_3$, $OCHF_2$ or $CF_3$.

2. The compound of claim 1, wherein $R_1$ is acetyl group.
3. The compound of claim 1, wherein L is a bond or one or a combination of two to five groups selected from:

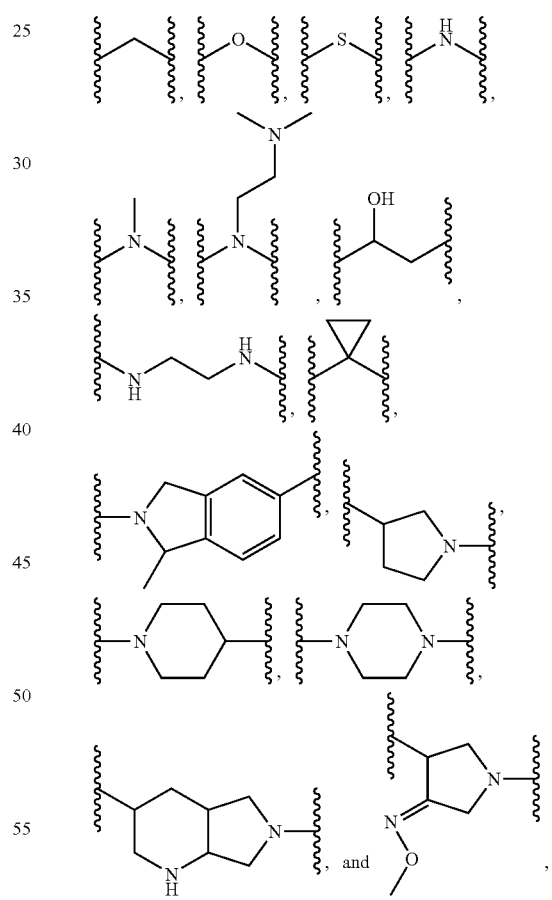

wherein the combination does not contain consecutive heteroatoms.

4. A compound as defined by claim 1 selected from the following compounds:
a. (R)-5'-[3-{1-(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-yl]-3'-hydroxy-benzoxazinorifamycin:

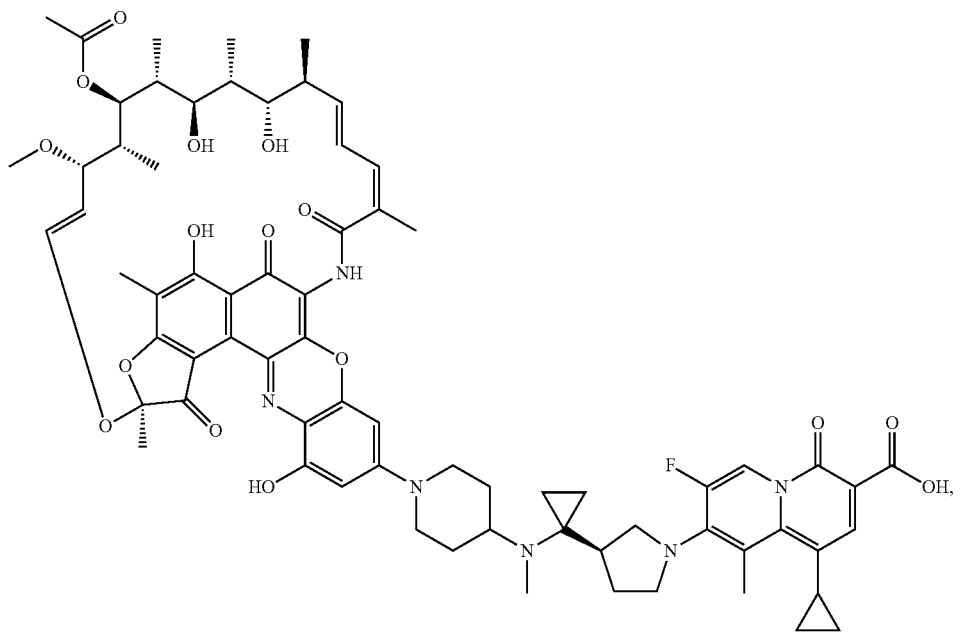
b. (R)-5'-[4-[1-[1-(3-Carboxy-1-cyclopropyl-6-fluoro-8-methoxy-4-oxo-1,4-dihydro-quinoline-7-yl)-pyrrolidin-3-yl-cyclopropyl-methyl]-amino]-piperidin-1-yl]-3'-hydroxy-benzoxazinorifamycin:
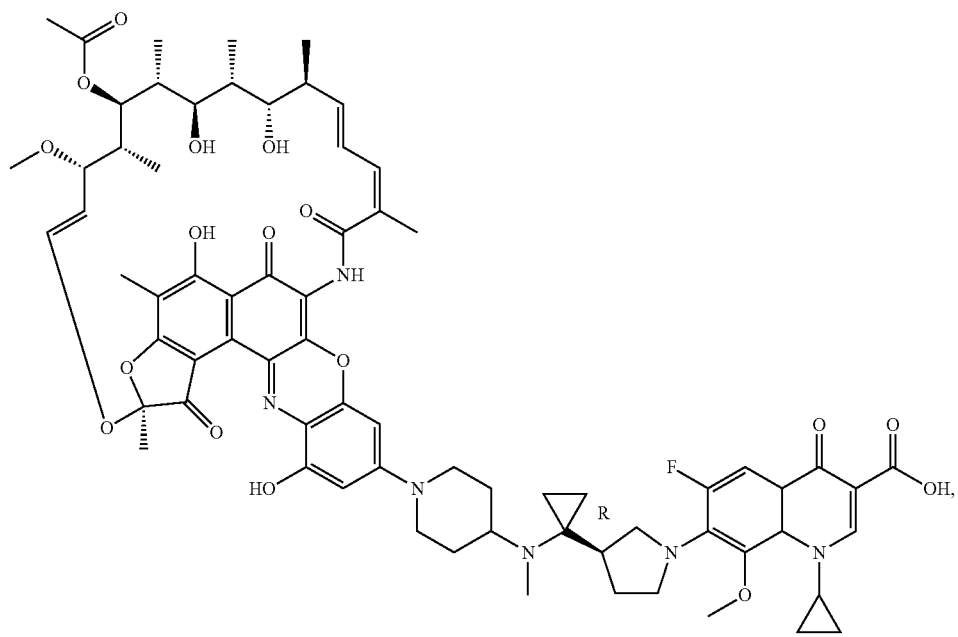

c. 5'-[4-(3-Carboxy-1-cyclopropyl-6-fluoro-8-methoxy-4-oxo-1,4-dihydroquinolin-7-yl)-piperazin-1-yl]-3'-hydroxy-benzoxazinorifamycin:
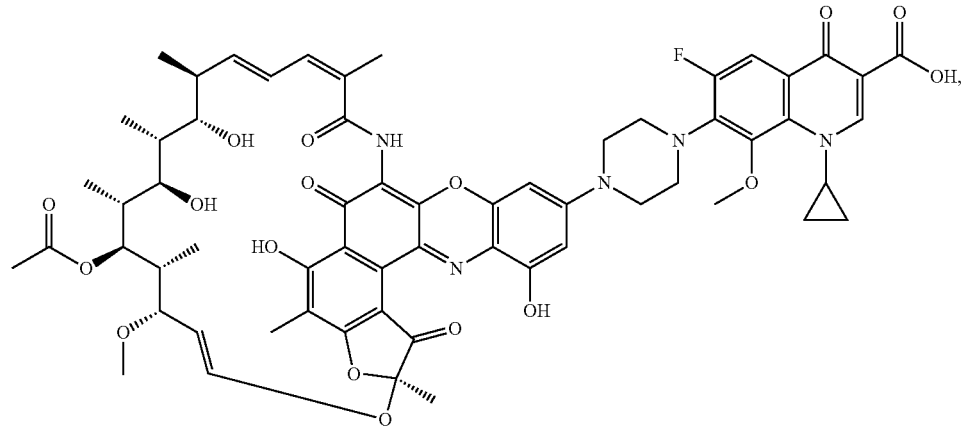
d. 5'-[4-[1-(3-Carboxy-1-cyclopropyl-6-fluoro-8-methoxy-4-oxo-1,4-dihydro-quinoline-7-yl)-piperidin-4-yl-amino]-piperidin-1-yl]-3'-hydroxy-benzoxazinorifamycin:
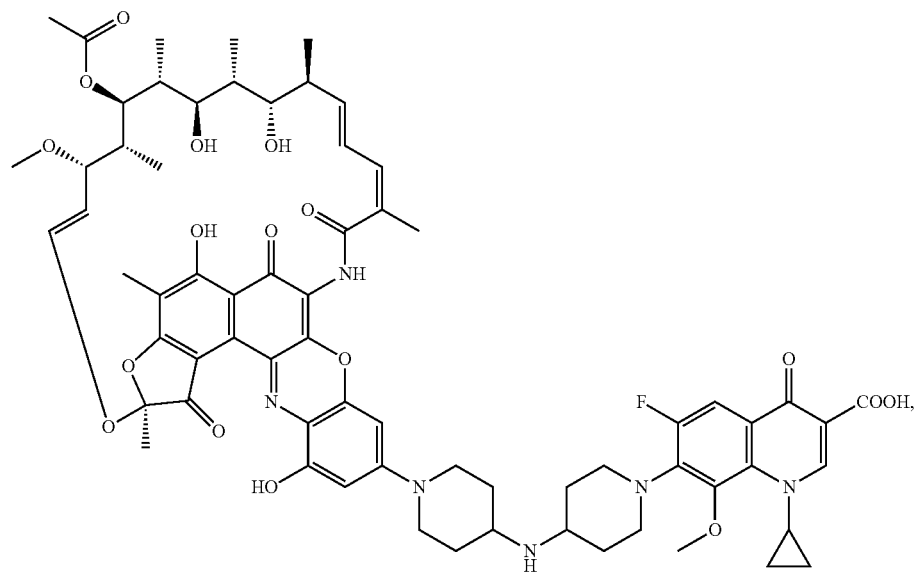

e. (R/S)-5'-[4-[[1-(1-Cyclopropyl-6-fluoro-8-methoxy-4-oxo-1,4-dihydro-quinolin-7-yl)-pyrrolidin-3-ylm-ethyl]-(2-dimethylamino-ethyl)-amino]-piperidin-1-yl]-3'-hydroxy-benzoxazinorifamycin:
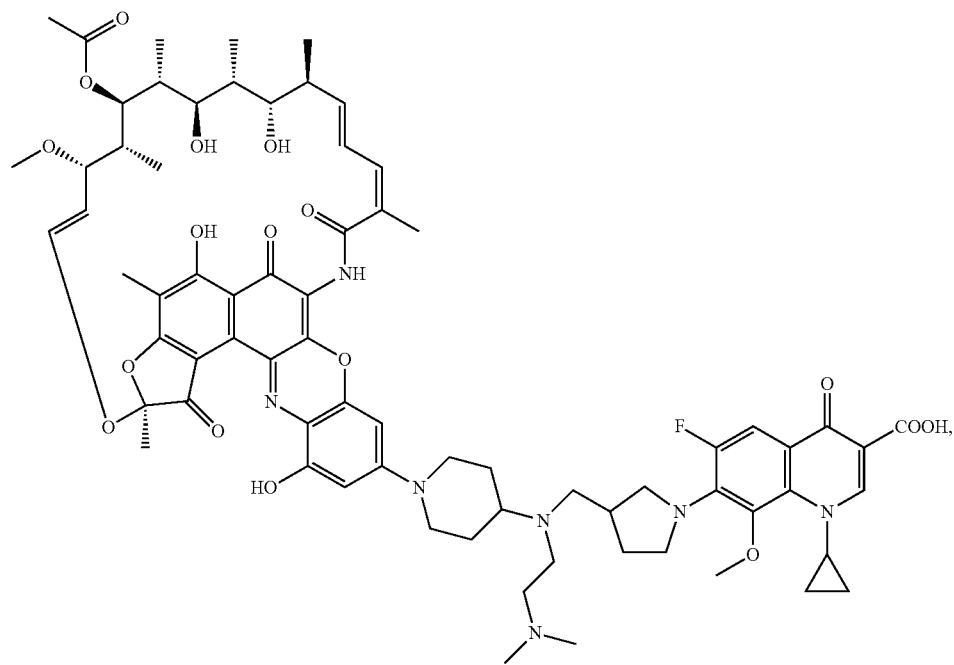
f. 4-Deoxy-3,4-[2-spiro-[1-(3-carboxy-1-cyclopropyl-6-fluoro-4-oxo-1,4-dihydroquinolin-7-yl)-piperidin-4-yl]]-(1H)-imidazo-(2,5-dihydro)rifamycin S:
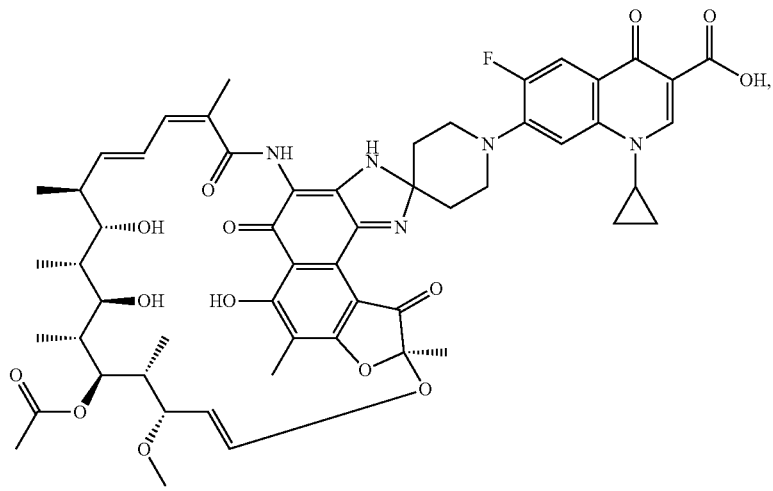

g. 4-Deoxy-3,4-[2-spiro-[1-(3-carboxy-1-cyclopropyl-6-fluoro-8-methoxy-4-oxo-1,4-dihydroquinolin-7-yl)-piperidin-4-yl]]-(1H)-imidazo-(2,5-dihydro)rifamycin S:

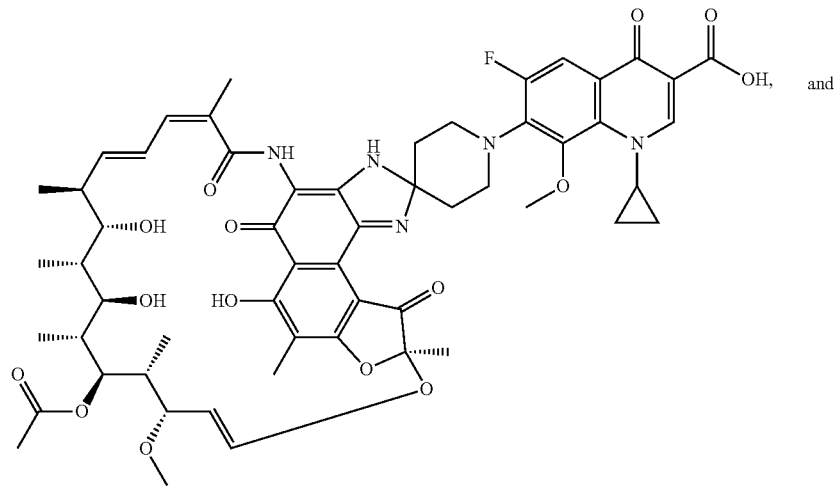
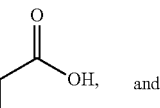

h. (R/S)-4-Deoxy-3,4-[2-spiro-[1-[1-(3-carboxy-1-cyclopropyl-6-fluoro-8-methoxy-4-oxo-1,4-dihydroquinolin-7-yl)-pyrrolidin-3-methyl]-piperidin-4-yl]]-(1H)-imidazo-(2,5-dihydro)rifamycin S:

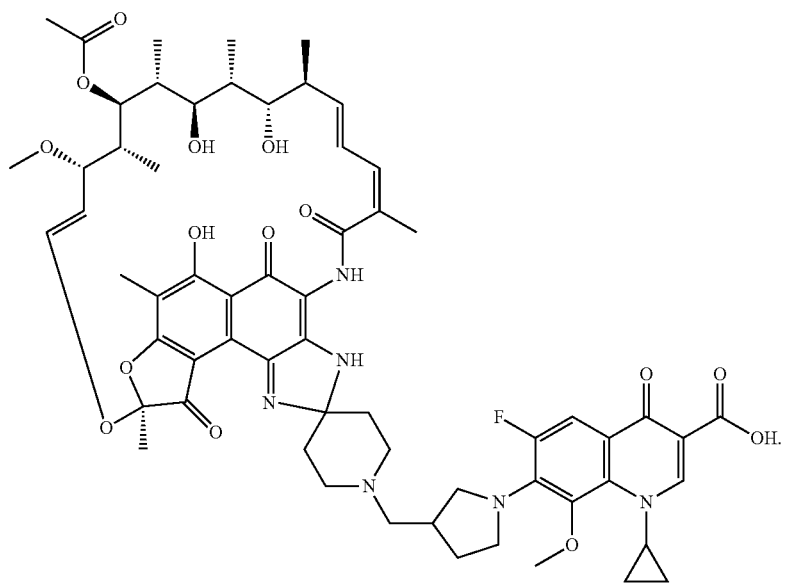

5. A pharmaceutical composition, useful as an antibacterial medicament, comprising a pharmaceutically effective amount of a compound in accordance with claim 1 in combination with a pharmaceutically acceptable carrier.

6. A method of treating a bacterial infection in a patient in need of such treatment by administering the pharmaceutical composition in accordance with claim 5.

* * * * *